(12) United States Patent
Remm et al.

(10) Patent No.: US 10,743,948 B2
(45) Date of Patent: Aug. 18, 2020

(54) SURGICAL TOOL WRISTS

(71) Applicant: Ethicon LLC, Guaynabo, PR (US)

(72) Inventors: Thomas B. Remm, Milford, OH (US); John A. Hibner, Mason, OH (US); Timothy J. Zimmer, Centerville, OH (US); Christopher William Long Birri, Cincinnati, OH (US)

(73) Assignee: Ethicon LLC, Cincinnati, OH (US)

( * ) Notice: Subject to any disclaimer, the term of this patent is extended or adjusted under 35 U.S.C. 154(b) by 775 days.

(21) Appl. No.: 15/371,764

(22) Filed: Dec. 7, 2016

(65) Prior Publication Data

US 2018/0153627 A1    Jun. 7, 2018

(51) Int. Cl.
*A61B 34/30* (2016.01)
*A61B 34/00* (2016.01)
*A61B 17/00* (2006.01)
*A61B 17/29* (2006.01)

(52) U.S. Cl.
CPC .............. *A61B 34/30* (2016.02); *A61B 34/71* (2016.02); *A61B 17/00234* (2013.01); *A61B 2017/00323* (2013.01); *A61B 2017/2938* (2013.01); *A61B 2034/305* (2016.02)

(58) Field of Classification Search
CPC ......... A61B 34/30; A61B 34/70; A61B 34/71; A61B 17/00234; A61B 17/28; A61B 17/282; A61B 17/29; A61B 2017/00292; A61B 2017/00353; A61B 2017/2926; A61B 2017/2927; A61B 2017/2929;
(Continued)

(56) References Cited

U.S. PATENT DOCUMENTS

| 8,114,345 B2 | 2/2012 | Dlugos, Jr. et al. |
| 8,771,270 B2 | 7/2014 | Burbank |
| 8,831,782 B2 | 9/2014 | Itkowitz |

(Continued)

FOREIGN PATENT DOCUMENTS

| WO | WO-2014151621 A1 | 9/2014 |
| WO | WO-2014151952 A1 | 9/2014 |

(Continued)

OTHER PUBLICATIONS

U.S. Appl. No. 15/200,283 entitled "Methods, Systems, and Devices for Initializing a Surgical Tool" filed Jul. 1, 2016.
(Continued)

*Primary Examiner* — Allen Porter
(74) *Attorney, Agent, or Firm* — Mintz Levin Cohn Ferris Glovsky and Popeo, P.C.

(57) ABSTRACT

Various exemplary surgical tool wrists are provided. In general, a surgical tool can include an elongate shaft and a wrist that couples an end effector to a distal end of the shaft. The surgical tool can include multiple elongate members configured to move, either individually or as a group of two or more of the elongate members, to cause movement of the end effector relative to the shaft. Each of the surgical tool's elongate members can be configured to extend along a helical path. Each of the elongate members can extend proximally from its associated helical path to a pulley at the wrist. The helical paths can be configured to guide the elongate members to approach and engage their respective pulleys at a substantially zero angle.

12 Claims, 23 Drawing Sheets

(58) Field of Classification Search
CPC .... A61B 2017/2932; A61B 2017/2938; A61B 2034/305; A61B 2034/306
See application file for complete search history.

(56) References Cited

U.S. PATENT DOCUMENTS

| | | | |
|---|---|---|---|
| 9,055,961 | B2 | 6/2015 | Manzo et al. |
| 10,463,437 | B2 * | 11/2019 | Chaplin ................. A61B 34/71 |
| 10,499,891 | B2 * | 12/2019 | Chaplin ........... A61B 17/00234 |
| 10,517,685 | B2 * | 12/2019 | Chaplin ................. A61B 34/37 |
| 2002/0111621 | A1 | 8/2002 | Wallace et al. |
| 2007/0255109 | A1 | 11/2007 | Stein et al. |
| 2011/0196419 | A1 | 8/2011 | Cooper |
| 2015/0051034 | A1 | 2/2015 | Cooper et al. |
| 2016/0338788 | A1 * | 11/2016 | Hares .................... A61B 34/71 |
| 2017/0007344 | A1 * | 1/2017 | Seow .................... A61B 34/71 |

FOREIGN PATENT DOCUMENTS

| | | | |
|---|---|---|---|
| WO | WO 2015/122944 | * | 8/2015 |
| WO | WO 2016/025132 | * | 2/2016 |

OTHER PUBLICATIONS

International Search Report and Written Opinion for PCT/IB2017/057074 dated Jan. 8, 2018 (17 pages).

Silke Schönherr: "Einfluss der seitlichen Seilablenkung auf die Lebensdauer von Drahtseilen beim Lauf über Seilscheiben," Aug. 1, 2005, XP055436695, Retrieved from the Internet URL:https://elib.uni-stuttgart.de/bitstream/11682/4070/1/D_Schoe.pdf.

* cited by examiner

SURGICAL TOOL WRISTS

FIELD

The present disclosure relates generally to surgical tool wrists.

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Various robotic systems have been developed to assist in MIS procedures. Robotic systems can allow for more intuitive hand movements by maintaining natural eye-hand axis. Robotic systems can also allow for more degrees of freedom in movement by including a "wrist" joint on the instrument, creating a more natural hand-like articulation. One drawback with robotic systems, however, is that cables extending through the wrist that are used for moving the instrument's end effector experience wear over time. The wear can lead to cable failure and/or reduced ability of the cables to generate the force needed to cause end effector movement while the cables withstand external load.

Accordingly, there remains a need for improved surgical tool wrists.

SUMMARY

In general, surgical tool wrists are provided.

In one aspect, a surgical tool is provided that in one embodiment includes an elongate shaft and an end effector coupled to a distal end of the elongate shaft. The end effector includes first and second channels. Each channel extends along a helical path. The surgical tool also includes a first elongate flexible member seated in the first channel and configured to be selectively moved to cause movement of the end effector, and a second elongate flexible member seated in the second channel and configured to be selectively moved to cause movement of the end effector.

The surgical tool can have any number of variations. For example, the end effector can be movable about a first pivot joint, the end effector can include first and second jaws that are movable relative to one another about a second pivot joint, the first and second elongate flexible members can be configured to be selectively moved to cause movement of the first and second jaws respectively about the second pivot joint. The first jaw can have the first channel formed therein, the second jaw can have the second channel formed therein, the first jaw can include a third channel, the second jaw can include a fourth channel, and the third and fourth channels can each extend along a helical path. The surgical tool can include a third elongate flexible member seated in the third channel and a fourth elongate flexible member seated in the fourth channel, the first and third elongate flexible members can be configured to be selectively moved to cause movement of the first jaw about the second pivot point, and the second and fourth elongate flexible members can be configured to be selectively moved to cause movement of the second jaw about the second pivot point. The first channel can have a diameter that is greater than a diameter of the third channel, the first and third elongate flexible members can have a substantially same diameter, the second channel can have a diameter that is greater than a diameter of the fourth channel, and the second and fourth elongate flexible members can have a substantially same diameter. The first, second, third, and fourth elongate flexible members can be configured to be selectively actuated to articulate the end effector about the first pivot point.

For another example, the end effector can be coupled to the elongate shaft at a wrist that includes a first pulley operatively engaged with the first elongate flexible member and a second pulley operatively engaged with the second elongate flexible member. The first elongate flexible member can approach and operatively engage the first pulley at a substantially zero-angle relative to a plane of the first pulley, and the second elongate flexible member can approach and operatively engage the second pulley at a substantially zero-angle relative to a plane of the second pulley.

For yet another example, each of the first and second elongate flexible members can include one of a cable, a wire, and a twisted string.

For still another example, the surgical tool can include a housing coupled to a proximal end of the elongate shaft. The housing can be configured to couple to a driver of a surgical robot configured to control the movement of the first and second elongate flexible members.

In another embodiment, a surgical tool is provided that includes an elongate shaft, an end effector coupled to the elongate shaft and having first and second jaws, and a wrist formed between the end effector and the elongate shaft. The wrist includes first and second pulleys, and the wrist is configured to allow articulation of the end effector relative to the elongate shaft. The surgical tool also includes a first elongate flexible member operatively engaged with the first pulley and the first jaw, and a second elongate flexible member operatively engaged with the second pulley and the second jaw. Movement of the first elongate flexible member is effective to cause movement of the end effector, and the first elongate flexible member has a substantially zero fleet angle with the first pulley throughout an entire range of articulation of the end effector. Movement of the second elongate flexible member is effective to cause articulation of the end effector, and the second elongate flexible member has a substantially zero fleet angle with the second pulley throughout the entire range of articulation of the end effector.

The surgical tool can vary in any number of ways. For example, the first and second elongate flexible members can each extend proximally from the end effector toward their respectively associated first and second pulleys at a non-zero angle relative to a longitudinal axis of the end effector throughout the entire range of the articulation of the end effector.

For another example, the first jaw can have a first helical groove formed therein that seats the first elongate member and guides the first elongate member proximally from the first jaw, and the second jaw can have a second helical groove formed therein that seats the second elongate member and guides the second elongate member proximally from the second jaw.

For yet another example, the first pulley can have a first groove formed along a circumference thereof seating the first elongate flexible member therein, the first elongate flexible member can have the substantially zero fleet angle with the first pulley regardless of whether or not the end effector is articulated relative to a longitudinal axis of the elongate shaft, the second pulley can have a second groove formed along a circumference thereof seating the second elongate flexible member therein, and the second elongate flexible member can have the substantially zero fleet angle with the second pulley regardless of whether the end effector is articulated relative to the longitudinal axis of the elongate shaft. The first and second pulleys can each have a face defining a plane that is substantially parallel to the longitudinal axis of the elongate shaft.

For yet another example, the surgical tool can include a third elongate flexible member operatively engaged with the first jaw, and a fourth elongate flexible member operatively engaged with the second jaw. The third elongate flexible member can be effective to cause movement of the end effector, the wrist can include a third pulley operatively engaged with the third elongate flexible member, and the third elongate flexible member can have a substantially zero fleet angle with the third pulley throughout the entire range of the articulation of the end effector. The fourth elongate flexible member can be effective to cause movement of the end effector, the wrist can include a fourth pulley operatively engaged with the fourth elongate flexible member, and the fourth elongate flexible member can have a substantially zero fleet angle with the fourth pulley throughout the entire range of the articulation of the end effector.

For still another example, each of the first and second elongate flexible members can include one of a cable, a wire, and a twisted string.

For yet another example, the surgical tool can include a housing coupled to a proximal end of the elongate shaft. The housing can be configured to couple to a driver of a surgical robot configured to control the movement of the first and second elongate flexible members.

In another aspect, a surgical method is provided that in one embodiment includes causing movement of a first elongate flexible member seated in a first channel formed in an end effector of a surgical tool. The movement of the first elongate flexible member causes the end effector to move relative to an elongate shaft having the end effector at a distal end thereof. The first channel extends along a helical path, and the first elongate flexible member extends proximally from the first channel to operatively engage a first pulley of the surgical tool at a substantially zero fleet angle.

The surgical method can vary in any number of ways. For example, the method can also include causing movement of a second elongate flexible member seated in a second channel formed in the end effector. The movement of the second elongate flexible member can cause the end effector to move relative to the elongate shaft. The second channel can extend along a helical path, and the second elongate flexible member can extend proximally from the second channel to operatively engage a second pulley of the surgical tool at a substantially zero fleet angle.

For another example, the first elongate flexible member can be movably seated in a first groove formed along a circumference of the first pulley, and the second elongate flexible member can be movably seated in a second groove formed along a circumference of the second pulley. The movement of the first elongate flexible member can cause the first elongate flexible member to move in the first groove along a first axis that is substantially parallel to a longitudinal axis of the elongate shaft. The movement of the second elongate flexible member can cause the second elongate flexible member to move in the second groove along a second axis that is substantially parallel to the longitudinal axis of the elongate shaft.

BRIEF DESCRIPTION OF DRAWINGS

This invention will be more fully understood from the following detailed description taken in conjunction with the accompanying drawings, in which.

DETAILED DESCRIPTION

Figure 1:
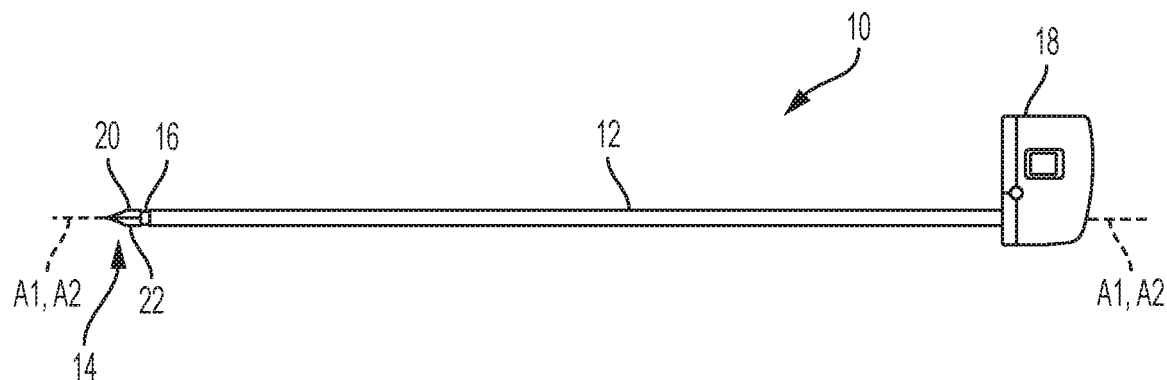
FIG. 1 is a side schematic view of one embodiment of a surgical tool.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes includes various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

Various exemplary surgical tool wrists are provided. In general, a surgical tool can include an elongate shaft and a wrist that couples an end effector to a distal end of the shaft. The wrist can be configured to facilitate movement of the end effector relative to the shaft. The surgical tool can include multiple elongate members (e.g., cables, wires, etc.) configured to move, either individually or as a group of two or more of the elongate members, to cause movement of the end effector relative to the shaft. The movement of the end effector can include articulation and opening/closing. In an exemplary embodiment, the end effector is configured to articulate and to open/close, though the end effector can be configured to only articulate or to only open/close. Articulation generally refers to movement of the end effector between an unarticulated, substantially zero-angle position, in which the end effector is substantially longitudinally aligned with the shaft, and an articulated position, in which the end effector is angularly orientated relative to the shaft. A person skilled in the art will appreciate that an angle may not be precisely zero but nevertheless be considered to be substantially zero due to any number of factors, such as manufacturing tolerance and precision of measurement devices. Opening/closing generally refers to movement of the end effector between an open position, in which opposed jaws of the end effector are open, and a closed position, in which the jaws are closed.

Each of the surgical tool's elongate members can be configured to extend along a helical path. In other words, the elongate members can each extend along a path that is angularly offset from the end effector's longitudinal axis. Each of the elongate members can extend proximally from its associated helical path to a pulley at the wrist that can be configured to facilitate smooth, controlled movement of its associated elongate member. The helical paths can be configured to guide the elongate members to approach and engage their respective pulleys at a substantially zero angle regardless of whether or not the end effector is articulated and regardless of whether or not the end effector is in the open position or the closed position. In other words, the helical paths can be configured to minimize a fleet angle between the elongate members and their respective pulleys. The elongate members each approaching and engaging their respective pulleys at a substantially zero angle, e.g., the fleet angle being substantially zero, may minimize friction between the elongate members and their respective pulleys, thereby helping to reduce wear on the elongate members and consequently increase their effective working life.

FIG. 1 illustrates one embodiment of a surgical tool 10 that includes an elongate shaft (also referred to herein as a "shaft") 12, an end effector 14, a wrist 16 that couples the end effector 14 to the shaft 12 at a distal end of the shaft 12, and a tool housing 18 coupled to a proximal end of the shaft 12. The end effector 14 is configured to move relative to the shaft 12 at the wrist 16, e.g., by pivoting at the wrist 16, to position the end effector 14 at a desired location relative to a surgical site during use of the tool 10. The housing 18 includes various components configured to control the operation of various features associated with the end effector 14 (e.g., any one or more of clamping, firing, rotation, articulation, energy delivery, etc.). In at least some embodiments, the shaft 12, and hence the end effector 14 coupled thereto, is configured to rotate about a longitudinal axis A1 of the shaft 12. In such embodiments, the various components of the housing 18 are configured to control the rotational movement of the shaft 12. In at least some embodiments, as in this illustrated embodiment, the surgical tool 10 is configured to releasably couple to a robotic surgical system, and the tool housing 18 can include coupling features configured to allow the releasable coupling of the tool 10 to the robotic surgical system. Each of the shaft 12 end effector 14, wrist 16, and housing 18 are discussed further below.

The surgical tool 10 can have any of a variety of configurations. In general, the surgical tool 10 can be configured to perform at least one surgical function and can include any of, for example, forceps, a grasper, a needle driver, scissors, an electrocautery tool that applies energy, a stapler, a clip applier, a suction tool, an irrigation tool, an imaging device (e.g., an endoscope or ultrasonic probe), etc. The surgical tool 10 in at least some embodiments is configured to apply energy (such as radiofrequency (RF) energy) to tissue, while in other embodiments the tool 10 is not configured to apply energy to tissue.

The shaft 12 can have any of a variety of configurations. In general, the shaft 12 is an elongate member extending distally from the housing 18 and having at least one inner lumen extending therethrough. The shaft 12 is fixed to the housing 18, but in other embodiments the shaft 12 can be releasably coupled to the housing 18 such that the shaft 12 can be interchangeable with other shafts. This may allow a single housing 18 to be adaptable to various shafts having different end effectors.

The end effector 14 can have a variety of sizes, shapes, and configurations. The end effector 14 in this illustrated embodiment includes a tissue grasper having a pair of opposed jaws 20, 22 configured to move between open and closed positions with one or both of the jaws 20, 22 configured to pivot at the wrist 16 to move the end effector 14 between the open and closed positions. The end effector 14 can have other configurations, e.g., scissors including a pair of opposed cutting jaws, a babcock including a pair of opposed grasping jaws, a retractor, etc.

Figure 2:
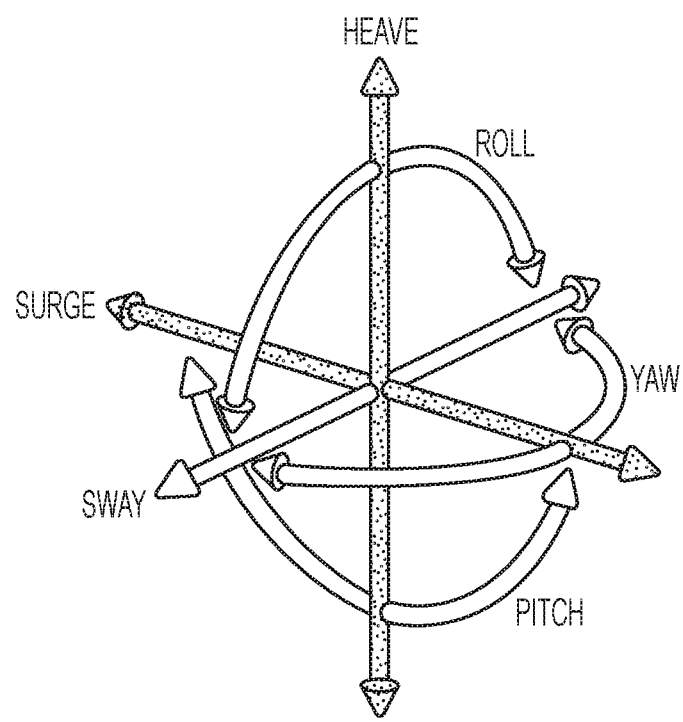
FIG. 2 is a graphical representation of terminology associated with six degrees of freedom.

The wrist 16 can have any of a variety of configurations. Exemplary embodiments of a wrist of a surgical tool are described in International Patent Publication No. WO 2014/151952 entitled "Compact Robotic Wrist" filed on Mar. 13, 2014, International Patent Publication No. WO 2014/151621 entitled "Hyperdexterous Surgical System" filed on Mar. 13, 2014, and U.S. patent application Ser. No. 15/200,283 entitled "Methods, Systems, And Devices For Initializing A Surgical Tool" filed on Jul. 1, 2016, which are hereby incorporated by reference in their entireties. In general, the wrist 16 can include a joint configured to allow movement of the end effector 14 relative to the shaft 12, such as a pivot joint at which the jaws 20, 22 are pivotally attached. In some embodiments, the pivoting motion can include pitch movement about a first axis of the wrist 16 (e.g., a X axis), yaw movement about a second axis of the wrist 16 (e.g., a Y axis), and combinations thereof to allow for 360° rotational movement of the end effector 14 about the wrist 16. In other embodiments, the pivoting motion can be limited to movement in a single plane, e.g., only pitch movement about the first axis of the wrist 16 or only yaw movement about the second axis of the wrist 16, such that end effector 14 rotates in a single plane. FIG. 2 illustrates degrees of freedom of a system represented by three translational or position variables, e.g., surge, heave, sway, and by three rotational or orientation variables, e.g., Euler angles or roll, pitch, yaw, that describe the position and orientation of a component of a surgical system with respect to a given reference Cartesian frame. As used herein, and as illustrated in FIG. 2, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right.

The surgical tool 10 includes a plurality of elongate members (obscured in FIG. 1) configured to effect the movement of the end effector 14 relative to the shaft 12. The elongate members are operably coupled to the tool housing 18, extend along the shaft 12, extend through the wrist 16, and are operably engaged with the end effector 14. In an exemplary embodiment, the elongate members extend distally from the tool housing 18 along the shaft 12 within an inner lumen of the shaft 12. The elongate members can be selectively actuated to cause the end effector 14 (e.g., one or both of the jaws 20, 22) to move (e.g., pivot) relative to the shaft 12. The selective actuation of the elongate members can cause any one or more of the elongate members to move, e.g., translate longitudinally, to cause the end effector 14 movement. The one or more of the elongate members that translate depend on the requested movement, e.g., the appropriate one or more of the elongate members translate longitudinally to cause the end effector 14 to articulate (e.g., both of the jaws 20, 22 angle in a same direction), to cause the end effector 14 to open (e.g., one or both of the jaws 20, 22 move away from the other of the jaws 20, 22), or to cause the end effector 14 to close (e.g., one or both of the jaws 20, 22 move toward the other of the jaws 20, 22). The actuation can be accomplished in any of a variety of ways, such as by actuating an actuator operably coupled to the tool housing 18, as discussed further below. In general, the actuation applies tension to the one or more of the elongate members in a proximal direction to cause the one or more of the elongate members to translate and thereby cause the end effector 14 to move relative to the shaft 12. In other words, the actuation pulls the one or more of the elongate members proximally. When both of the jaws 20, 22 are configured to move to open and close the end effector 14, at least one of the elongate members can be operably coupled to one of the jaws 20 to move that jaw 20 and at least one other of the flexible members can be operably coupled to the other one of the jaws 22 to move that jaw 22. When only one of the jaws 20, 22 is configured to move to open and close the end effector 14, at least one of the elongate members can be operably coupled to that one of the jaws 20, 22 to move that one of the jaws 20, 22.

The plurality of elongate members can have a variety of configurations, for example cables, wires, or twisted strings. The elongate members can be made from any of a variety of materials, such as a metal (e.g., Tungsten, stainless steel, etc.). In an exemplary embodiment, the elongate members are each flexible. Exemplary embodiments of elongate members of a surgical tool are described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014.

The movement of the end effector 14 caused by movement of one or more of the flexible members includes movement of the end effector 14 between an unarticulated position, in which the end effector 14 is substantially longitudinally aligned with the shaft 12 (e.g., a longitudinal axis A2 of the end effector 14 is substantially aligned with the longitudinal axis A1 of the shaft 12 such that the end effector 14 is at a substantially zero angle relative to the shaft 12), and an articulated position, in which the end effector 14 is angularly orientated relative to the shaft 12 (e.g., the longitudinal axis A2 of the end effector 14 is angled relative to the longitudinal axis A1 of the shaft 12 such that the end effector 14 is at a non-zero angle relative to the shaft 12). A person skilled in the art will appreciate that the end effector 14 may not be precisely aligned with the shaft 12 (e.g., may not be at a precise zero angle relative thereto) but nevertheless be considered to be substantially aligned with the shaft 12 (e.g., be at a substantially zero angle) due to any number of factors, such as manufacturing tolerance and precision of measurement devices. The end effector 14 is shown in the unarticulated position in FIG. 1.

The tool 10 includes a plurality of pulleys (obscured in FIG. 1) at the wrist 16 that are positioned proximal to the end effector 14. Each of the pulleys is operatively engaged with one of the elongate flexible members. Each of the elongate flexible members extends proximally from the end effector 14 at a non-zero angle relative to the end effector's longitudinal axis A1 to approach and engage its associated one of the pulleys at a substantially zero angle, regardless of whether or not the end effector 14 is articulated and regardless of whether or not the end effector 14 is open or closed. In other words, a fleet angle between an elongate flexible member and its associated pulley can be substantially zero regardless of whether or not the end effector 14 is articulated and regardless of whether or not the end effector 14 is open or closed. The elongate flexible members having substantially zero fleet angles with their respective pulleys may help reduce friction and accordant stress on the elongate flexible members since they approach and engage their respective pulleys at a consistent, optimal angle that reduces rubbing between the two engaged elements.

The tool housing 18 can have any of a variety of configurations. In general, the tool housing 18 can include one or more actuation mechanisms at least partially disposed therein configured to cause movement of the plurality of elongate members and thereby cause movement of the end effector 14 about the wrist 16. The one or more actuation mechanisms can include, for example, one or more movement mechanisms operably coupled to the plurality of flexible members, such as pulley(s) configured to be moved to cause translation of the elongate members. The tool housing 18 is configured to be releasably attached to a robotic surgical system (also referred to herein as a "robot" or "surgical robot") so as to releasably attach the tool 10 to the robot. The tool housing 18 can be configured to releasably attach to a robot in any of a variety of ways, as will be appreciated by a person skilled in the art, such as by clamping thereto, clipping thereto, or slidably mating therewith. The one or more movement mechanisms are configured to be controlled by the robot, as will be appreciated by a person skilled in the art, such as by the robot including one or more motors operably coupled to one or more inputs of the tool housing 18 that are operably coupled to the one or more movement mechanisms. The robot includes a computer system that can receive user inputs and can control the motor(s) in response to the user inputs and hence control movement of the elongate members and consequently movement of the end effector 14.

The tool driver to which the tool housing 18 is configured to removably and replaceably couple can have any of a variety of configurations. Exemplary embodiments of tool drivers configured to removably and replaceably couple to a surgical tool such as the surgical tool 10 of FIG. 1 and other embodiments of surgical tools described herein are described in previously mentioned U.S. patent application Ser. No. 15/200,283 entitled "Methods, Systems, And Devices For Initializing A Surgical Tool" filed on Jul. 1, 2016. Also, exemplary embodiments of a tool housing of a surgical tool including one or more actuation mechanisms and configured to releasably attach to a robotic surgical system are described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014. Exemplary embodiments of robotic surgical systems are described in U.S. Pat. No. 8,831,782 entitled "Patient-Side Surgeon Interface For A Teleoperated Surgical Instrument" filed Jul. 15, 2013, which is hereby incorporated by reference in its entirety, and in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014.

In other embodiments, instead of being configured to releasably couple to a robotic surgical system, the tool housing 18 can be configured to be handheld by a user during use of the tool 10. The tool housing 18 in these embodiments can include a trigger, lever, or other actuator configured to be manually or electronically manipulated to cause movement of the flexible elongate members, as will be appreciated by a person skilled in the art.

Figure 3:
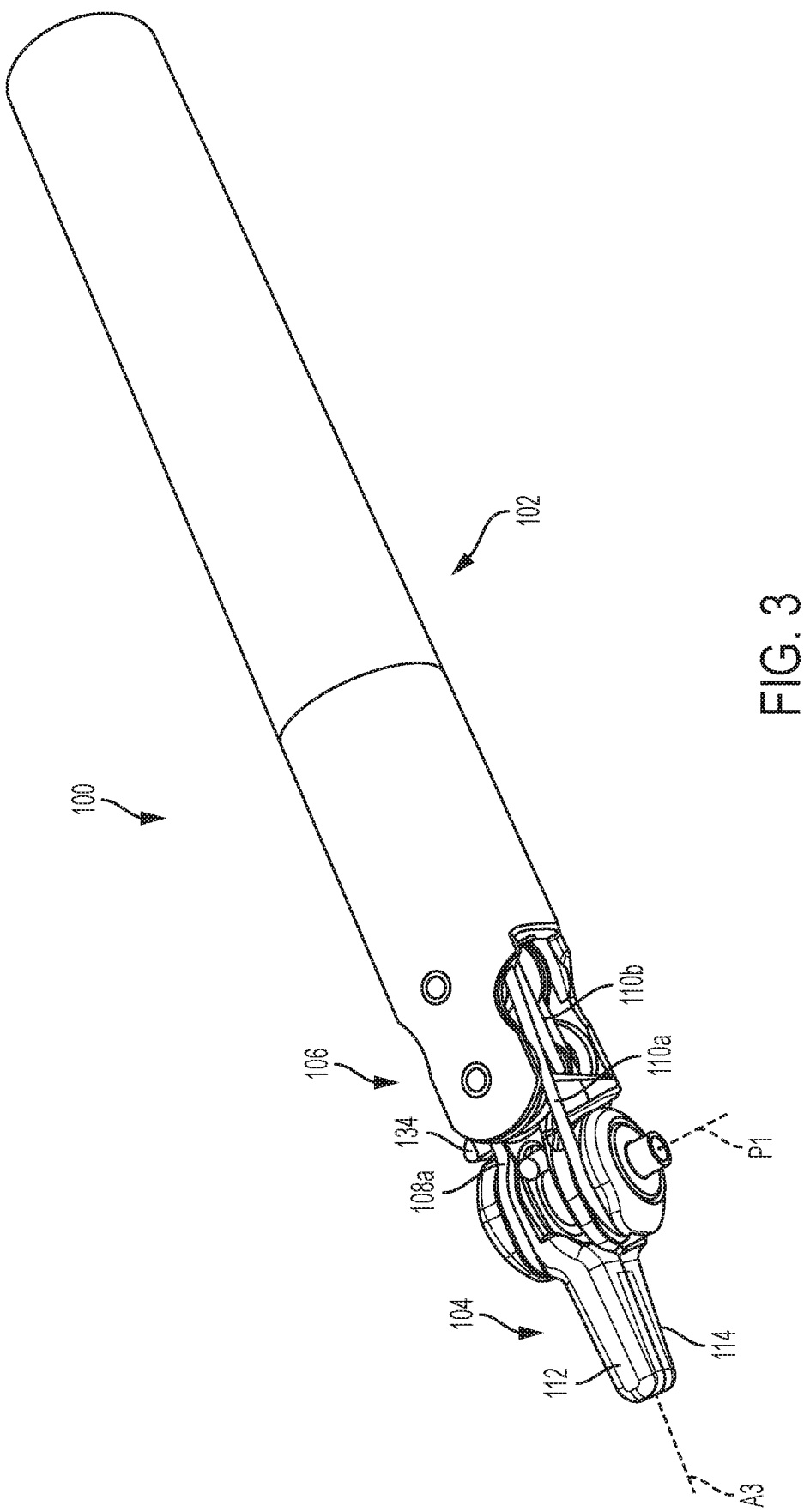
FIG. 3 is a perspective view of one embodiment of a surgical tool having a wrist.

FIG. 3 illustrates an exemplary embodiment of a surgical tool 100 that includes an elongate shaft 102, an end effector 104 including a pair of opposed jaws 112, 114, a wrist 106 that couples the end effector 104 to the shaft 102 at a distal end of the shaft 102, a plurality of elongate flexible members 108a, 108b, 110a, 110b, a first plurality of pulleys 116a, 116b, 118a, 118b (see FIG. 4) at the wrist 206, and a second plurality of pulleys 120a, 120b, 122a, 122b (see FIG. 4) at the wrist 106. The tool 100 is generally configured and used similar to the tool 10 of FIG. 1. FIG. 3 shows the end effector 104 in an unarticulated position and with the jaws 112, 114 closed. Only a distal portion of the tool 100 is shown in FIG. 3. The tool 100 can include a tool housing (not shown) coupled to a proximal end of the shaft 102. The tool housing can, as discussed herein, be configured to releasably and replaceably couple to a surgical robot that controls movement of the tool 100, or the tool housing can be configured to be handheld and manually controlled to control movement of the tool 100.

In this illustrated embodiment the flexible members 108a, 108b, 110a, 110b are in the form of cables, but as mentioned above, the flexible members 108a, 108b, 110a, 110b can have other configurations (e.g., wires, twisted strings, etc.). Only a distal portion of the flexible members 108a, 108b, 110a, 110b are shown in the figures for clarity of illustration. The flexible members 108a, 108b, 110a, 110b extend proximally from the end effector 104 to the tool housing configured to facilitate movement of the flexible members 108a, 108b, 110a, 110b, as discussed herein. The shaft 102 includes an inner lumen extending therethrough that receives the flexible members 108a, 108b, 110a, 110b therein. The inner lumen can be a single inner lumen or can include a number of independent lumens that each receive one of the flexible members 108a, 108b, 110a, 110b. Alternatively, the flexible members 108a, 108b, 110a, 110b can extend along the shaft 102 outside thereof, such as in longitudinal channels formed in an exterior surface of the shaft 102.

The tool 100 includes four flexible members 108a, 108b, 110a, 110b, one pair operatively coupled to each of the jaws 112, 114, but another number of flexible members can be used in other embodiments. For example, a surgical tool having an end effector that does not include a pair of jaws can include two flexible members configured to be moved to cause articulation of the end effector.

Figure 5:
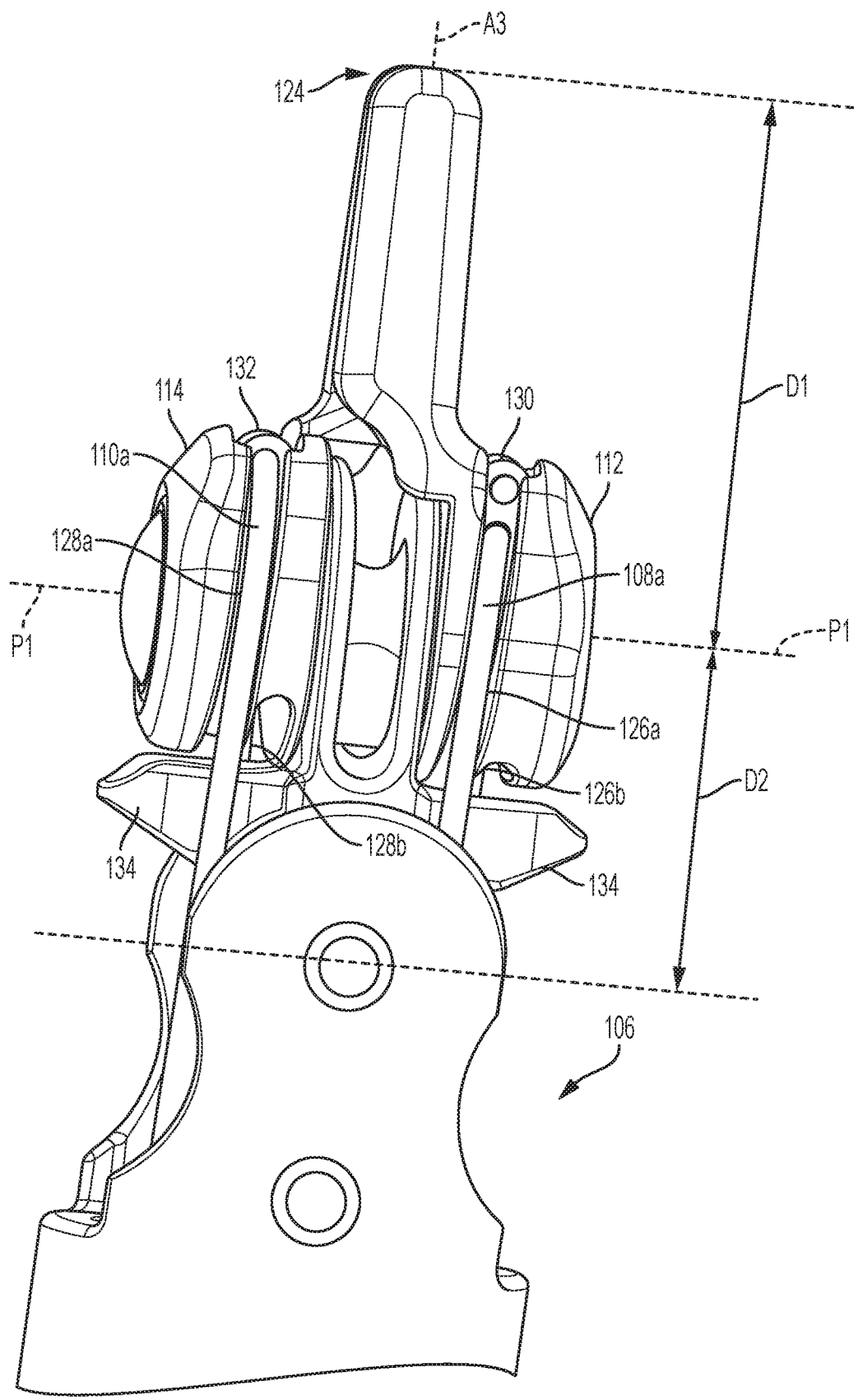
FIG. 5 is another side view of a distal portion of the surgical tool of FIG. 1.

As shown in FIGS. 3 and 5, the tool 100 has a first pivot axis P1 about which the jaws 112, 114 are configured to pivot relative to each other to move the end effector 104 between open and closed positions and about which the jaws 112, 114 are configured to move together to articulate the end effector 104. The first pivot axis P1 is substantially perpendicular to a longitudinal axis A3 of the end effector 104. A person skilled in the art will appreciate that axes may not be precisely perpendicular to one another but nevertheless be considered to be substantially perpendicular due to any number of factors, such as manufacturing tolerance and precision of measurement devices. The tool 100 has two joints at the first pivot axis P1, one joint for each of the jaws 112, 114. In other words, the first jaw 112 is configured to pivot about the first pivot axis P1 at one of the two joints, and the second jaw 114 is configured to pivot about the first pivot axis P1 at the other one of the two joints. Having two joints allows the jaws 112, 114 to each move relative to one another. Actuation of the flexible members 108a, 108b, 110a, 110b is configured to cause the movement of the first jaw 112 at its associated joint at the first pivot axis P1 and of the second jaw 114 at its associated joint at the first pivot axis P1. In an exemplary embodiment, the jaws 112, 114 are configured to pivot in tandem at their respective joints. In other words, during opening of the jaws 112, 114 each of the jaws 112, 114 rotates at its associated joint, and during closing of the jaws 112, 114 each of the jaws 112, 114 rotates at its associated joint.

Figure 4:
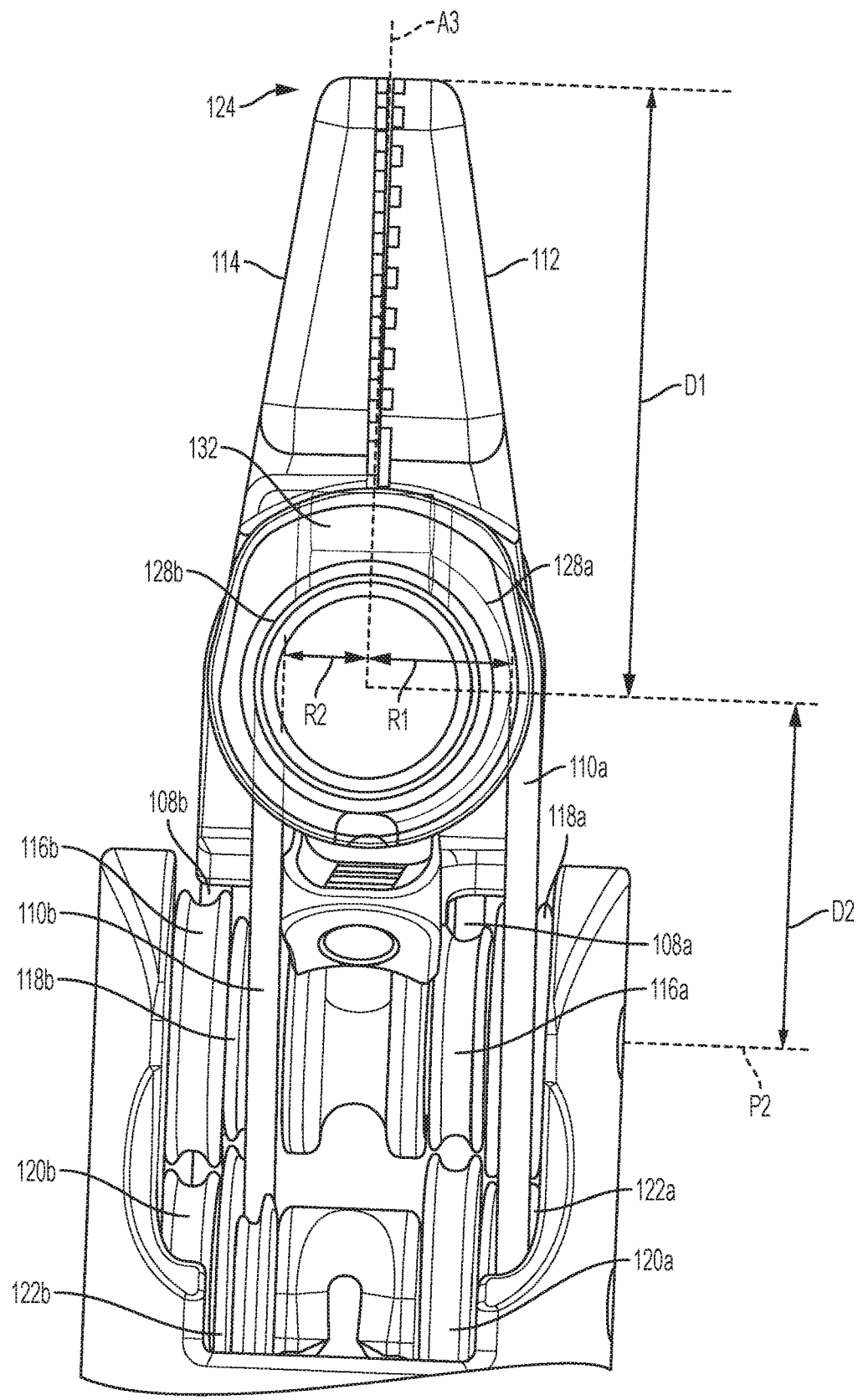
FIG. 4 is a side, partially transparent view of a distal portion of the surgical tool of FIG. 1.

As shown in FIG. 4, the tool 100 has a second pivot axis P2 at the wrist 106 about which the end effector 104 (e.g., the jaws 112, 114) is configured to articulate relative to the shaft 102. Actuation of the flexible members 108a, 108b, 110a, 110b is configured to cause the movement of the wrist 106 at the second pivot axis P2, and hence to cause articulation of the end effector 104, as discussed herein. The end effector 104 is thus configured to articulate with multiple degrees of freedom, e.g., a degree of freedom by articulating about the first pivot axis P1 and another degree of freedom by articulating about the second pivot axis P2. The wrist 106 in this illustrated embodiment is configured to pivot about the second pivot axis P2 in a single plane, e.g., in one of pitch and yaw. The end effector 104 in this illustrated embodiment is configured to pivot about the first pivot axis P1 in a single, different plane, e.g., the other of pitch and yaw.

Figures 6, 7:
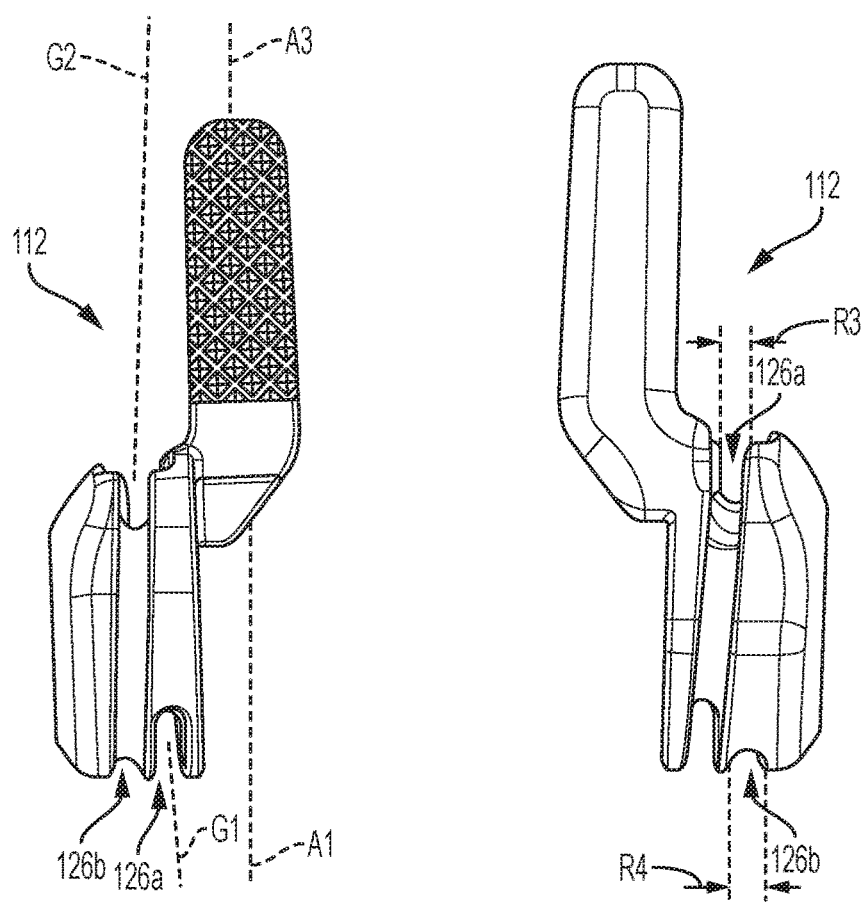
FIG. 6 is a side view of a first jaw of the surgical tool of FIG. 1.
FIG. 7 is another side view of the first jaw of FIG. 6.
Figure 8:
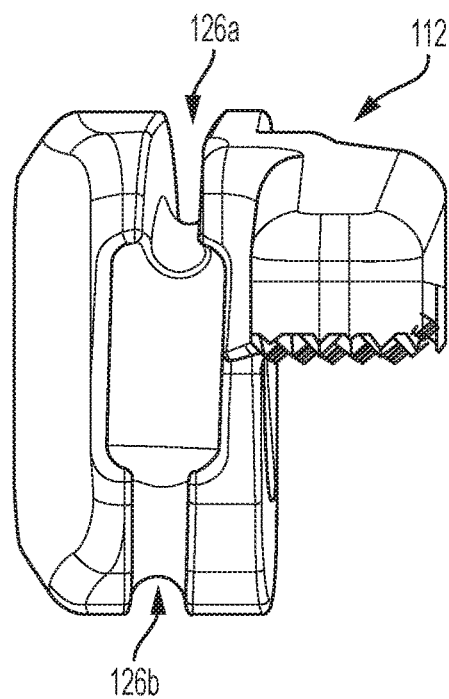
FIG. 8 is an end view of the first jaw of FIG. 6.
Figure 9:
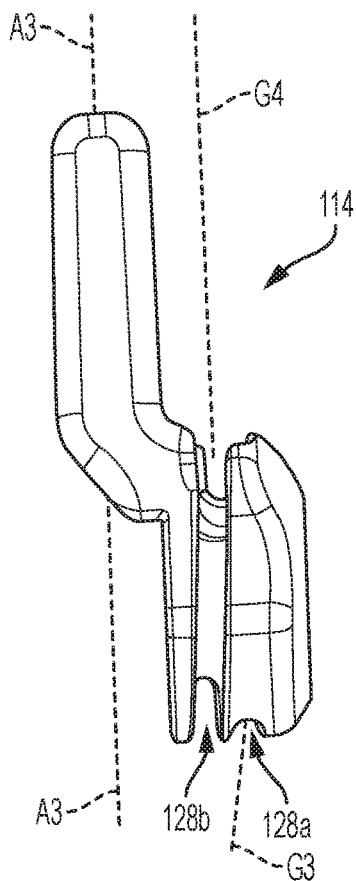
FIG. 9 is a side view of a second jaw of the surgical tool of FIG. 1.
Figure 10:
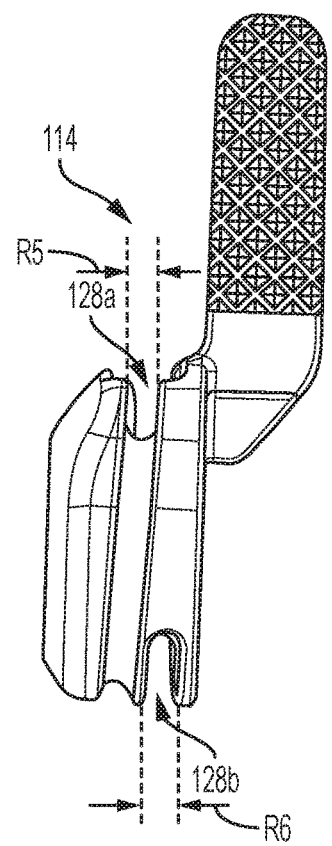
FIG. 10 is another side view of the second jaw of FIG. 9.
Figure 11:
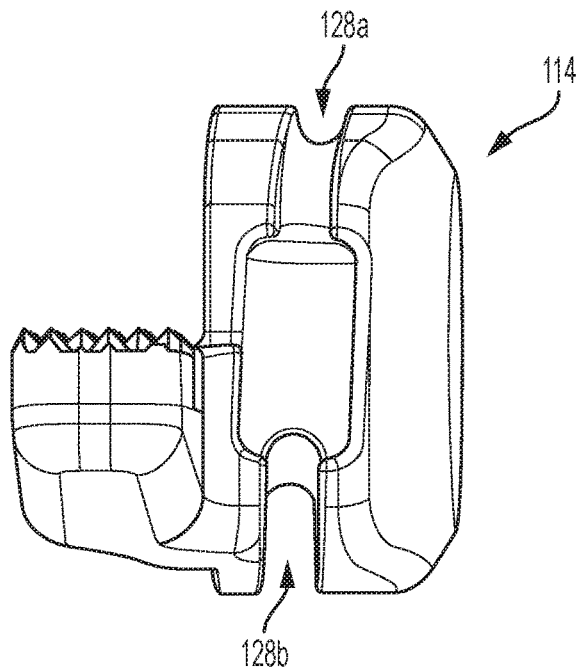
FIG. 11 is an end view of the second jaw of FIG. 9.

As shown in FIGS. 4-11, the end effector 104 has a plurality of grooves 126a, 126b, 128a, 128b formed therein that each seat therein one of the flexible members 108a, 108b, 110a, 110b. FIGS. 6-8 illustrate the first jaw 112 as a standalone element, and FIGS. 9-11 illustrate the second jaw 114 as a standalone element. The first jaw 112 has a first pair of the grooves 126a, 126b formed therein that seat the first and second flexible members 108a, 108b, and the second jaw 114 has a second pair of the grooves 128a, 128b formed therein that seat the third and fourth flexible members 110a, 110b.

Each of the grooves 126a, 126b, 128a, 128b defines a helical path. The paths are each helical in that each groove has a helix shape. The helices each spiral around the first pivot axis P1. Since the first pivot axis P1 is substantially perpendicular to the longitudinal axis A3 of the end effector 104, the grooves 126a, 126b, 128a, 128b are thus each angularly offset from the end effector's longitudinal axis A3 regardless of whether or not the end effector 104 is articulated and, if the end effector 104 is articulated at a non-zero angle relative to the shaft's longitudinal axis A4, regardless of the non-zero angle at which the end effector 104 is articulated. The end effector's longitudinal axis A3 is aligned with the shaft's longitudinal axis A4 when the end effector 104 is unarticulated, as shown in FIG. 3, so the grooves 126a, 126b, 128a, 128b are also each angularly offset from the shaft's longitudinal axis A4 when the end effector 104 is unarticulated. Also, each of the grooves 126a, 126b, 128a, 128b is not in a single longitudinal plane parallel to the end effector's longitudinal axis A3 due to their helix shape that extends substantially perpendicular to the end effector's longitudinal axis A3. FIG. 6 shows an angle G1 of the first groove 126a and an angle G2 of the second groove 126b each offset at a non-zero angle from the end effector's longitudinal axis A3. The angles G1, G2 are substantially the same as one another. Similarly, FIG. 9 shows an angle G3 of the third groove 128a and an angle G4 of the fourth groove 128b each offset at a non-zero angle from the end effector's longitudinal axis A3. The angles G3, G4 are substantially the same as one another.

As shown in FIGS. 4, 5, and 12-16, each of the flexible members 108a, 108b, 110a, 110b extends proximally from the end effector 104 along the helical path of its respective groove 126a, 126b, 128a, 128b to the wrist 106 and the shaft 102. In other words, the grooves 126a, 126b, 128a, 128b guide the flexible members 108a, 108b, 110a, 110b away from the end effector 104 along the helical path defined by the helix shapes of the grooves 126a, 126b, 128a, 128b. The flexible members 108a, 108b, 110a, 110b thus each extend proximally from the end effector 104 along a path that is angularly offset from the end effector's longitudinal axis A3 regardless of whether or not the end effector 104 is articulated and, if the end effector 104 is articulated at a non-zero angle relative to the shaft's longitudinal axis A4, regardless of the non-zero angle at which the end effector 104 is articulated.

In an exemplary embodiment, the two grooves 126a, 126b formed in the first jaw 112 have different diameters from one another, and the flexible members 108a, 108b seated therein have a substantially same diameter as one another. The flexible members 108a, 108b can have any of a variety of diameters, for example 0.019 mm. The different diameters of the first jaw's grooves 126a, 126b may reflect that the first and second flexible members 108a, 108b respectively seated in the first and second grooves 126a, 126b can experience different loads or tensions. In an exemplary embodiment, the diameter of each of the grooves 126a, 126b is approximately equal to the diameter of each of the flexible members 108a, 108b seated therein, which may help reduce friction by limiting lateral movement of the flexible members 108a, 108b within their respective grooves 126a, 126b. A person skilled in the art will appreciate that the diameters may not be precisely equal but nevertheless be considered to be approximately equal due to any number of factors, such as manufacturing tolerance and precision of measurement devices.

Figure 12:
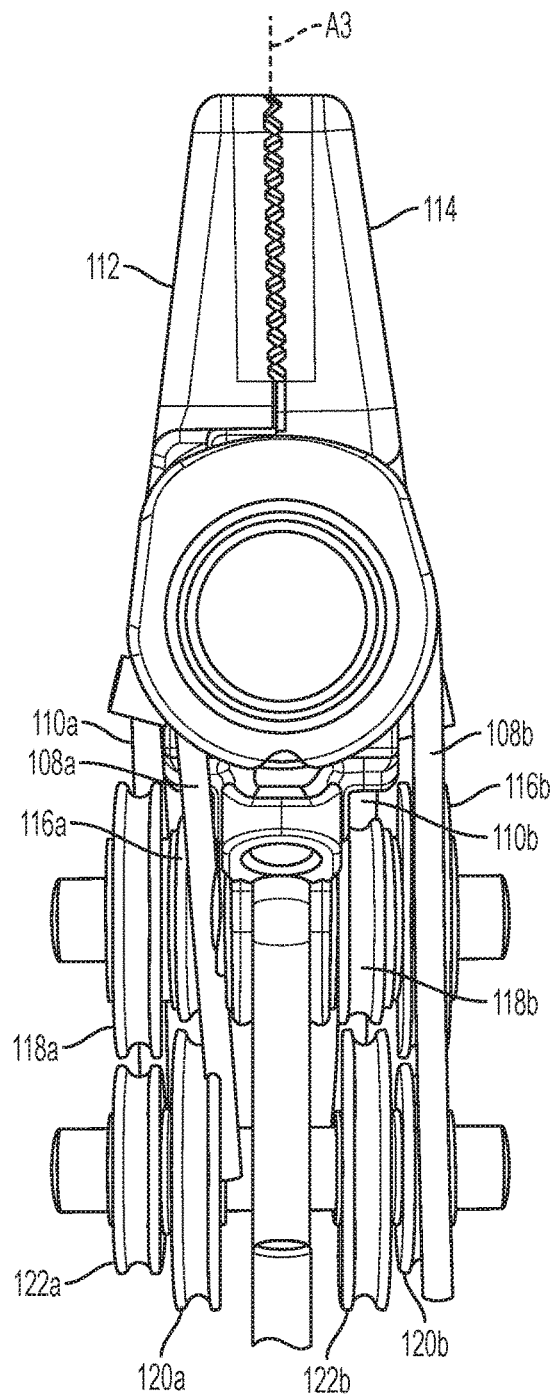
FIG. 12 is a side view of a distal portion of the surgical tool of FIG. 1 with a shaft of the surgical tool omitted for clarity of illustration.
Figure 13:
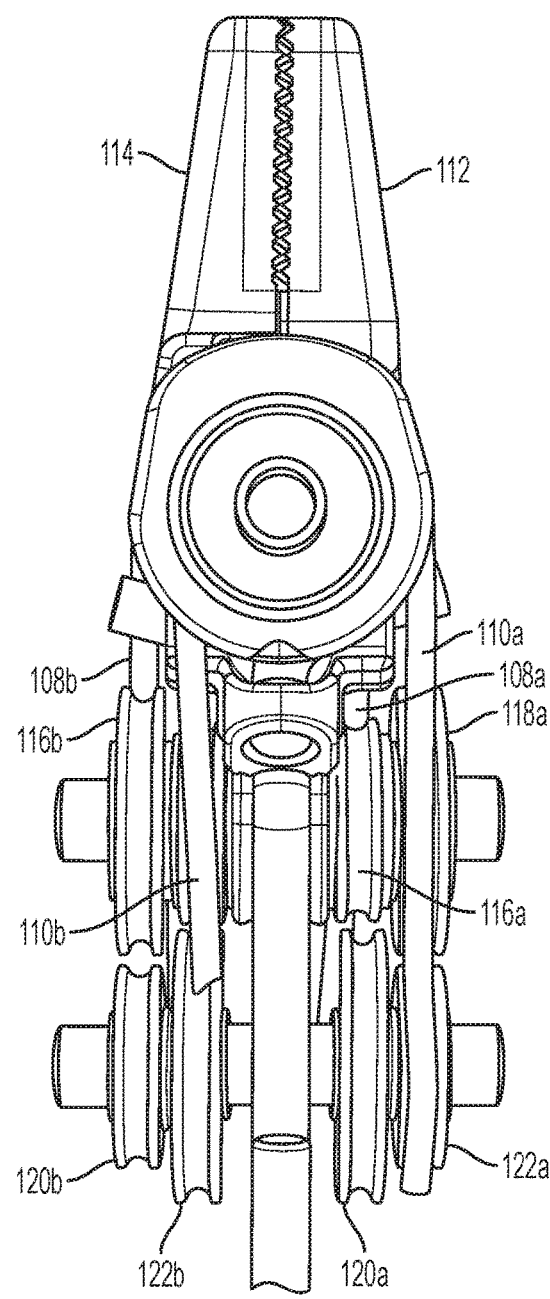
FIG. 13 is another side view of the distal portion of the surgical tool of FIG. 12.
Figure 14:
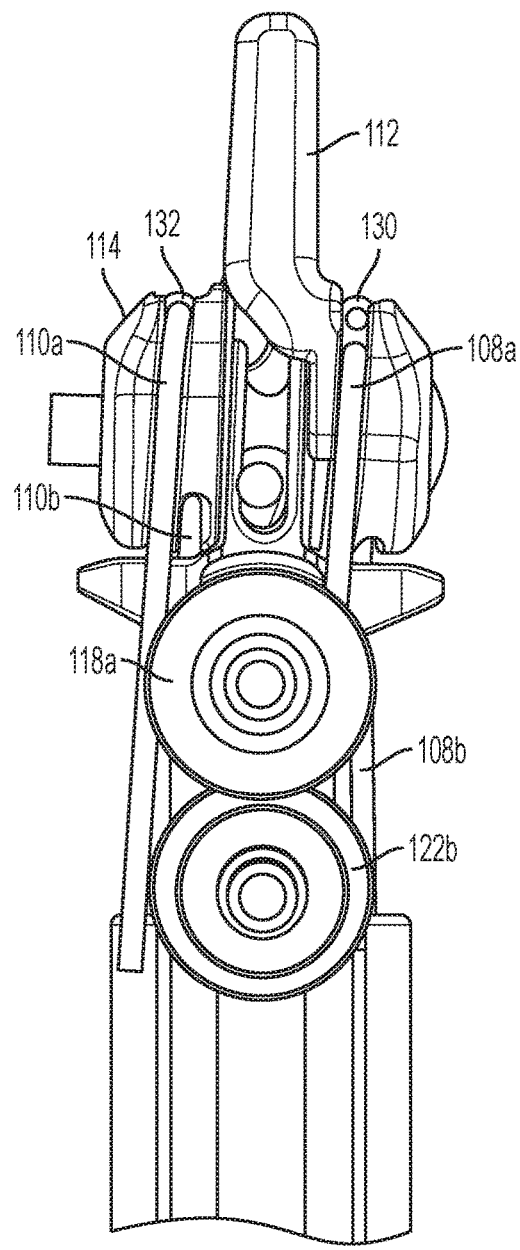
FIG. 14 is yet another side view of the distal portion of the surgical tool of FIG. 12.
Figure 15:
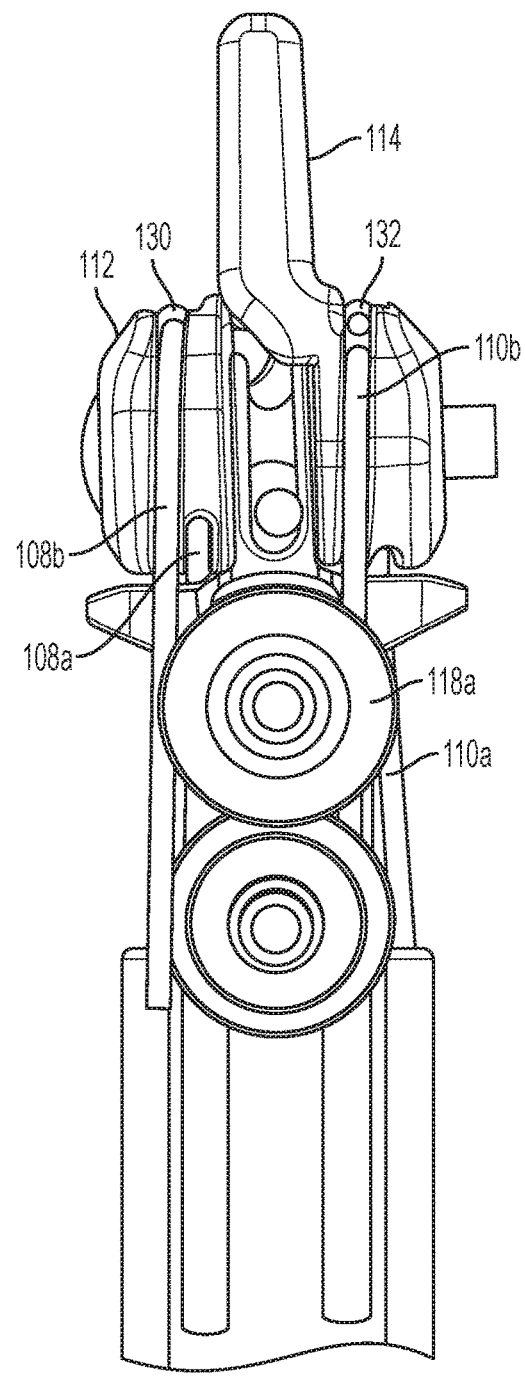
FIG. 15 is still another side view of the distal portion of the surgical tool of FIG. 12.
Figure 16:
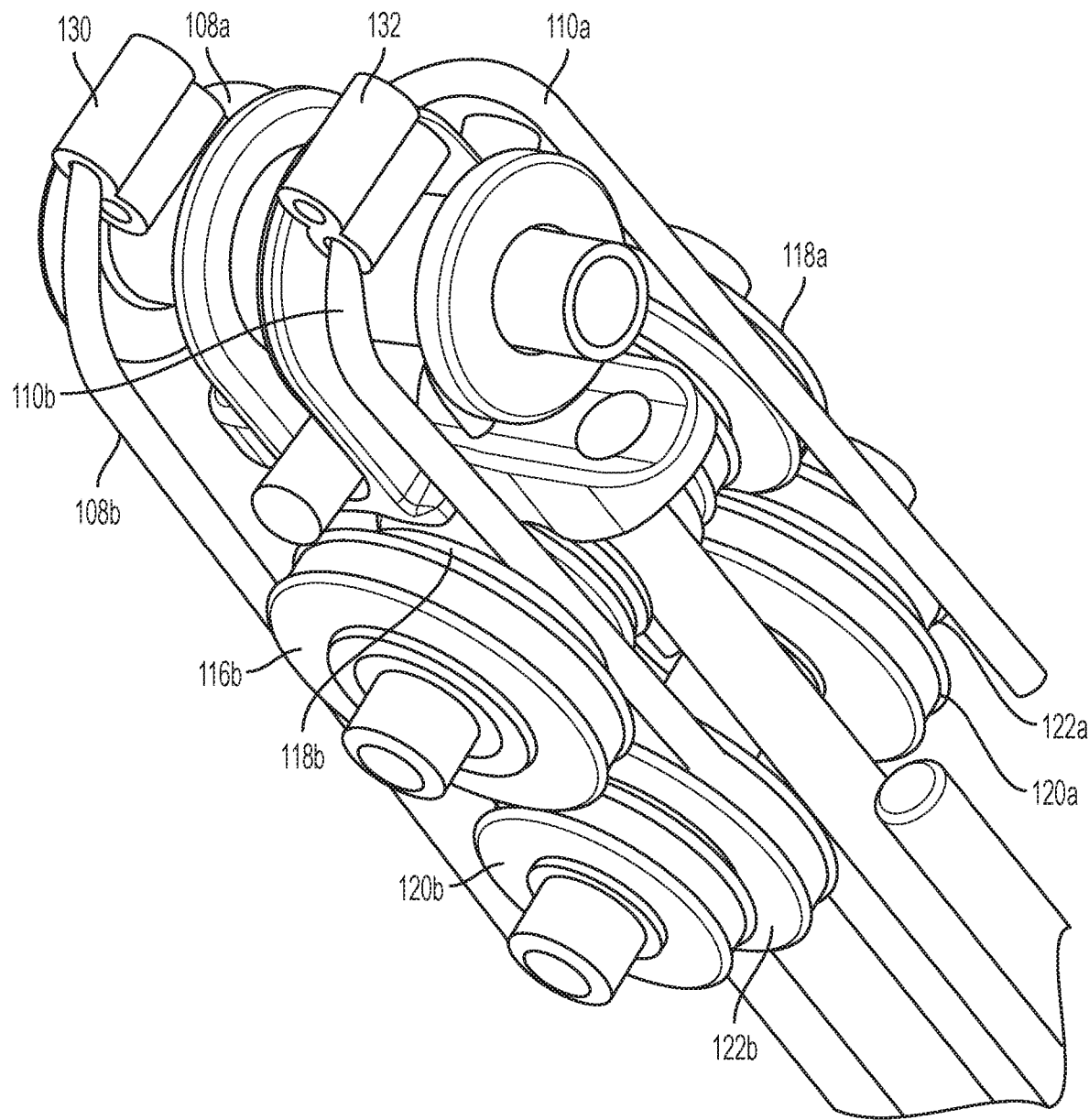
FIG. 16 is a perspective view of a portion of the surgical tool of FIG. 1 with the shaft and an end effector of the surgical tool omitted for clarity of illustration.

As shown in FIG. 7, the first jaw's first groove 126a that seats the first flexible member 108a therein has a diameter R3, which is less than a diameter R4 of the first jaw's second groove 126b that seats the second flexible member 108b therein. The second flexible member 108b typically experiences a higher load or tension than the first flexible member 108a when closing the end effector 104 and/or when the end effector 104 is clamping tissue and/or other material between its jaws 112, 114 because the second flexible member 108b is acting to pull the first jaw 112 toward the second jaw 114 and has to provide enough force to securely clamp tissue and/or other material that is between the jaws 112, 114. FIG. 12 demonstrates this arrangement, where the second flexible member 108b by its position relative to the first and second jaws 112, 114 is typically pulled in a proximal direction with more tension than the first flexible member 108a experiences in order to urge the first jaw 112 toward the second jaw 114.

Similar to the first jaw's grooves 126a, 126b, in an exemplary embodiment, the two grooves 128a, 128b formed in the second jaw 114 have different diameters from one another, and the flexible members 110a, 110b seated therein have a substantially same diameter as one another. As shown in FIG. 10, the second jaw's first groove 128a that seats the third flexible member 110a therein has a diameter R5, which is greater than a diameter R6 of the second jaw's second groove 128b that seats the fourth flexible member 110b therein. As demonstrated by FIGS. 4 and 13, the third flexible member 110a typically experiences a higher load or tension than the fourth flexible member 110b when closing the end effector 104 and/or when the end effector 104 is clamping tissue and/or other material between its jaws 112, 114 because the third flexible member 110a is acting to pull the second jaw 114 toward the first jaw 112 and has to provide enough force to securely clamp tissue and/or other material that is between the jaws 112, 114. In another exemplary embodiment, grooves formed in a surgical tool's end effector and configured to seat elongate flexible members therein can each have a same diameter.

The grooves 126a, 126b, 128a, 128b guiding each of the flexible members 108a, 108b, 110a, 110b along a helical path allows the flexible members 108a, 108b, 110a, 110b to approach and engage their respective pulleys 116a, 116b, 118a, 118b at a substantially zero angle. This substantially zero angle approach and engagement may thus be achieved regardless of whether or not the end effector 104 is articulated and, if the end effector 104 is articulated at a non-zero angle relative to the shaft's longitudinal axis A2, regardless of the non-zero angle at which the end effector 104 is articulated. As mentioned above, the flexible members 108a, 108b, 110a, 110b approaching and engaging their respective pulleys 116a, 116b, 118a, 118b at the substantially zero angle, such that the fleet angle is substantially zero, may minimize friction between the flexible members 108a, 108b, 110a, 110b and their respective pulleys 116a, 116b, 118a, 118b, thereby helping to reduce wear on the flexible members 108a, 108b, 110a, 110b and thus increase their effective working life. The larger diameter R4 of the second groove 126b seating the second flexible member 108b and the larger diameter R5 of the third groove 128a seating the third flexible member 110a may allow for lateral movement of the second and third flexible members 108b, 110a in their respective grooves 116b, 118a and thereby help maintain the substantially zero fleet angle between the second and third flexible members 108b, 110a and their associated pulleys 116b, 118a throughout an entire range of the end effector's articulation, e.g., when the end effector 104 is at any angular position up to and including its maximum non-zero angled position.

The flexible members 108a, 108b, 110a, 110b as cables are typically formed of numerous individual filaments that may each be individually worn down and/or broken due to friction against their associated pulley 116a, 116b, 118a, 118b and accordingly contribute to overall wear on the flexible member. By maintain the substantially zero fleet angle, fewer of the filaments will wear down and/or break, thereby improving overall flexible member life.

Each of the pulleys 116a, 116b, 118a, 118b has a channel extending around a circumference thereof that is configured to movably seat its associated one of the flexible members 108a, 108b, 110a, 110b therein. The flexible members 108a, 108b, 110a, 110b are configured to move in their respective pulley channels when moved to cause end effector 104 opening, closing, or articulation. Faces of each of the pulleys 116a, 116b, 118a, 118b defines a plane that is substantially aligned with the longitudinal axis A4 of the shaft 102 and, when the end effector 104 is unarticulated, with the longitudinal axis A3 of the end effector 104. The channels are therefore each substantially aligned with the longitudinal axis A4 of the shaft 102 and, when the end effector 104 is unarticulated, with the longitudinal axis A3 of the end effector 104. The flexible members 108a, 108b, 110a, 110b may thus extend along the shaft 102 to the housing without tangling with each other.

Each of the pulleys 116a, 116b, 118a, 118b can have a surface finish on at least the channels thereof that seat the flexible members 108a, 108b, 110a, 110b to reduce a coefficient of friction of the pulleys 116a, 116b, 118a, 118b and thereby further reduce friction between the pulleys 116a, 116b, 118a, 118b and their associated flexible members 108a, 108b, 110a, 110b.

The flexible members 108a, 108b, 110a, 110b extend linearly and proximally from their respective one of the first plurality of pulleys 116a, 116b, 118a, 118b to a respective one of the second plurality of pulleys 120a, 120b, 122a, 122b. The second plurality of pulleys 120a, 120b, 122a, 122b are oriented similar to the first plurality of pulleys 116a, 116b, 118a, 118b, e.g., with faces and channels thereof similarly aligned relative to the shaft 102. The grooves 126a, 126b, 128a, 128b are thus configured to similarly guide the flexible members 108a, 108b, 110a, 110b to their respective one of the second plurality of pulleys 120a, 120b, 122a, 122b at a substantially zero angle.

Distal ends of each of the flexible members 108a, 108b, 110a, 110b are in a fixed position relative to the jaws 112, 114 with which they are operatively coupled. As shown in FIGS. 4, 5, and 14-16, the first jaw 112 has coupled thereto a first double barrel element 130 that holds the distal ends of the first and second flexible members 108a, 108b in fixed positions relative to the first jaw 112 by crimping the distal ends in respective holes in the first double barrel element 130. Similarly, the second jaw 114 has coupled thereto a second double barrel element 132 that holds the distal ends of the third and fourth flexible members 110a, 110b in fixed positions relative to the second jaw 114 by crimping the distal ends in respective holes in the second double barrel element 132. Although the double barrel elements 130, 132 crimp the flexible members' distal ends, the flexible members' distal ends can be fixed thereto in other ways, such as by using adhesive, welding, etc. Further, the double barrel elements 130, 132 need not be used and the flexible members' distal ends can be fixed relative to their respective jaws 112, 114 in other ways, such as by using adhesive to adhere the distal ends directly to the jaws 112, 114, welding the distal ends directly to the jaws 112, 114, etc.

The grooves 126a, 126b, 128a, 128b guiding the flexible members 108a, 108b, 110a, 110b and the pulleys 116a, 116b, 118a, 118b seating the flexible members 108a, 108b, 110a, 110b can each help maximize mechanical advantage at the wrist 106. In general, maximizing mechanical advantage at the wrist 106 can help the end effector 104 (e.g., the jaws 112, 114 thereof) apply a sufficient amount of grip or compression force to tissue and/other material between the jaws 112, 114 while the end effector 104 (e.g., the jaws 112, 114 thereof) withstands an external load applied to an exterior thereof, such as by tissue and/or other matter pressing against an exterior surface of the end effector 104. Although the grip or compression force and the external load amounts can vary, in one example, the grip or compression force can be about four pounds, and the external load can be about two pounds.

Four parameters may affect the mechanical advantage at the wrist 106, as discussed below with respect to FIGS. 4 and 5. The first parameter is a first distance D1 extending between a distal tip 124 of the end effector 104 and the first pivot axis P1. Minimizing the first distance D1 improves the mechanical advantage, e.g., a smaller first distance D1 corresponds to a smaller radius of curvature for the pivot motion of the jaws 112, 114 that takes less force to achieve than with a larger radius of curvature. The end effector 104 should have enough length to effectively engage tissue and to be visible during use in a surgical procedure, so the distance D1 cannot be zero and can be a difficult parameter to optimize for mechanical advantage purposes given these constraints.

The second parameter is a second distance D2 extending between the first pivot axis P1 and the second pivot axis P2. Minimizing the second distance D2 improves the mechanical advantage, e.g., a smaller second distance D2 corresponds to a smaller radius of curvature for the articulating motion of the end effector 104 that takes less force to achieve than with a larger radius of curvature. The two pivot axes P1, P2 have distance therebetween, otherwise they would be coaxial and result in only one pivot axis instead of two, so the distance D2 cannot be zero and can be a difficult parameter to optimize for mechanical advantage purposes given these constraints.

The third parameter is a length of each of the flexible members 108a, 108b, 110a, 110b directly contacting the end effector 104. Maximizing these lengths improves the mechanical advantage, e.g., the force needed to move the end effector 104 can be distributed along more of the flexible members 108a, 108b, 110a, 110b. The flexible members 108a, 108b, 110a, 110b directly contact the end effector 104 in their respective grooves 126a, 126b, 128a, 128b such that the length of each of the flexible members 108a, 108b, 110a, 110b directly contacting the end effector 104 corresponds to a length of each of the flexible members 108a, 108b, 110a, 110b that is seated in their respective grooves 126a, 126b, 128a, 128b. The grooves 126a, 126b, 128a, 128b being helical can increase the length of each of the flexible members 108a, 108b, 110a, 110b directly contacting the end effector 104, as compared to non-helical grooves seating flexible members, and thereby improve the mechanical advantage. Also, the helix shape of the grooves 126a, 126b, 128a, 128b defines a diameter. The third parameter can thus also be expressed as a diameter defined by the grooves 126a, 126b, 128a, 128b. Maximizing these diameters thus improves the mechanical advantage. By way of example, FIG. 4 shows a diameter R1 defined by the third groove 128a seating the third flexible member 110a therein and a diameter R2 defined by the fourth groove 128b seating the fourth flexible member 110b therein.

The fourth parameter is a diameter of the pulleys 116a, 116b, 118a, 118b that the flexible members 108a, 108b, 110a, 110b respectively approach and engage as the flexible members 108a, 108b, 110a, 110b extend proximally from the end effector 104 from their respective grooves 126a, 126b, 128a, 128b. Maximizing these pulley diameters improves the mechanical advantage, e.g., the force needed to move the end effector 104 can be distributed along a longer length of the flexible members 108a, 108b, 110a, 110b. The grooves 126a, 126b, 128a, 128b being helical can allow the flexible members 108a, 108b, 110a, 110b to approach and engage their respective pulleys 116a, 116b, 118a, 118b at the substantially zero angle through the end effector's range of articulation, which may allow for larger size pulleys 116a, 116b, 118a, 118b since clearance room for the flexible members 108a, 108b, 110a, 110b need not be present adjacent the pulleys 116a, 116b, 118a, 118b. In other words, non-zero fleet angles need not be accommodated by the pulleys 116a, 116b, 118a, 118b.

Figure 17:
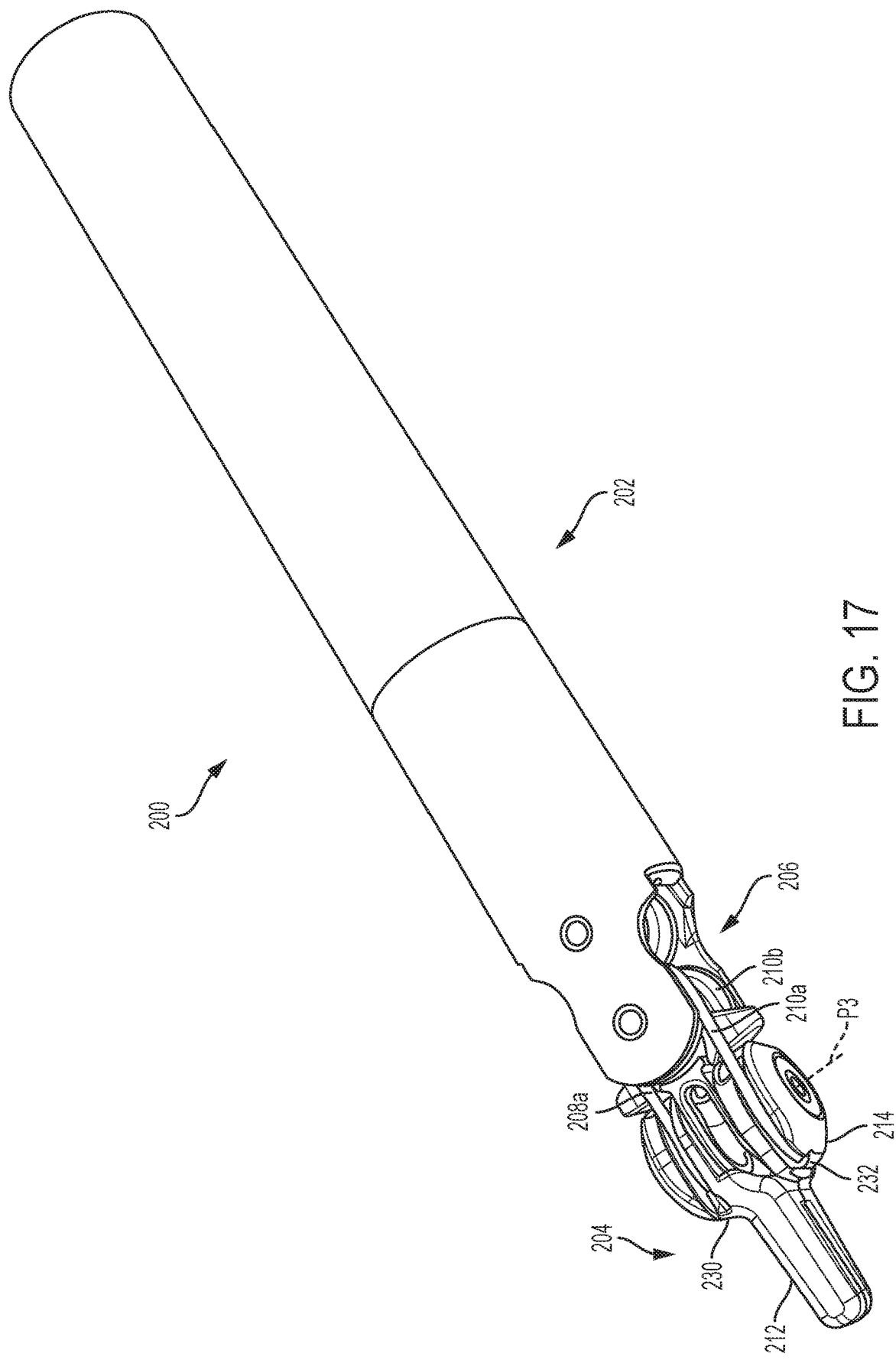
FIG. 17 is a perspective view of another embodiment of a surgical tool having a wrist and with an end effector of the surgical tool unarticulated and in a closed position.

FIG. 17 illustrates another exemplary embodiment of a surgical tool 200 that includes an elongate shaft 202, an end effector 204 including a pair of opposed jaws 212, 214, a wrist 206 that couples the end effector 204 to the shaft 202 at a distal end of the shaft 202, a plurality of elongate flexible members 208a, 208b, 210a, 210b, first and second double barrel members 230, 232, a first plurality of pulleys 216a, 216b, 218a, 218b (see FIGS. 18-21) at the wrist 206, and a second plurality of pulleys 220a, 220b, 222a, 222b (see FIGS. 18-21) at the wrist 206. The tool 200 is generally configured and used similar to the tool 100 of FIG. 3. The tool 200 can include a tool housing (not shown) coupled to a proximal end of the shaft 202. The tool 200 has a first pivot axis P3 about which the jaws 212, 214 are configured to pivot relative to each other to move the end effector 204 between open and closed positions and about which the jaws 212, 214 are configured to move together to articulate the end effector 204. The tool 200 also has a second pivot axis P4 at the wrist 206 about which the end effector 204 (e.g., the jaws 212, 214) is configured to articulate relative to the shaft 202.

In this illustrated embodiment the flexible members 208a, 208b, 210a, 210b are in the form of cables, but as mentioned above, the flexible members 208a, 208b, 210a, 210b can have other configurations. Only a distal portion of the flexible members 208a, 208b, 210a, 210b are shown in the figures for clarity of illustration.

Figure 18:
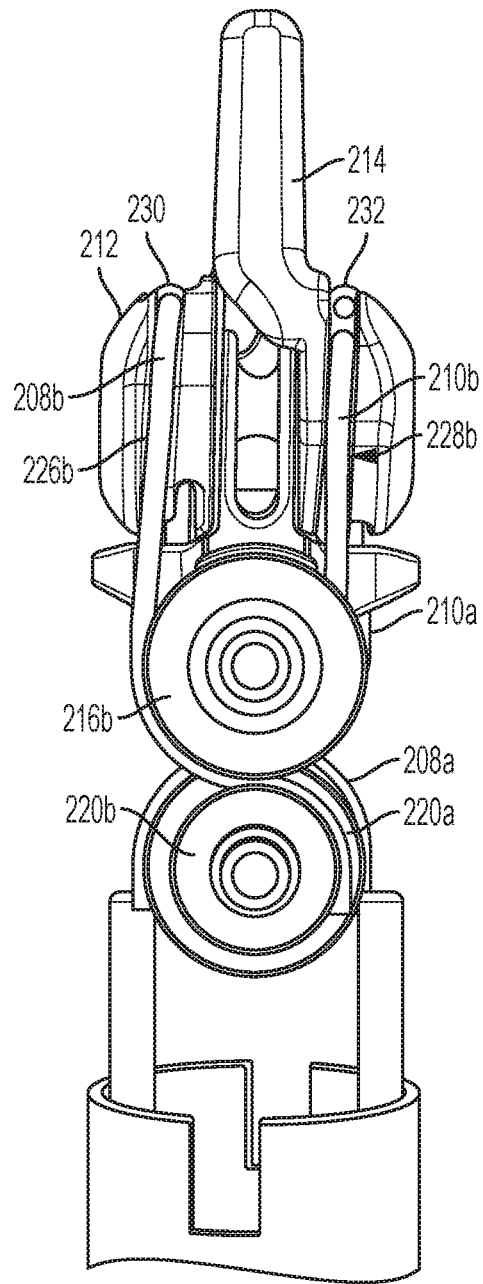
FIG. 18 is a side view of a distal portion of the surgical tool of FIG. 17 with a distal portion of a shaft of the surgical tool omitted for clarity of illustration.
Figure 19:
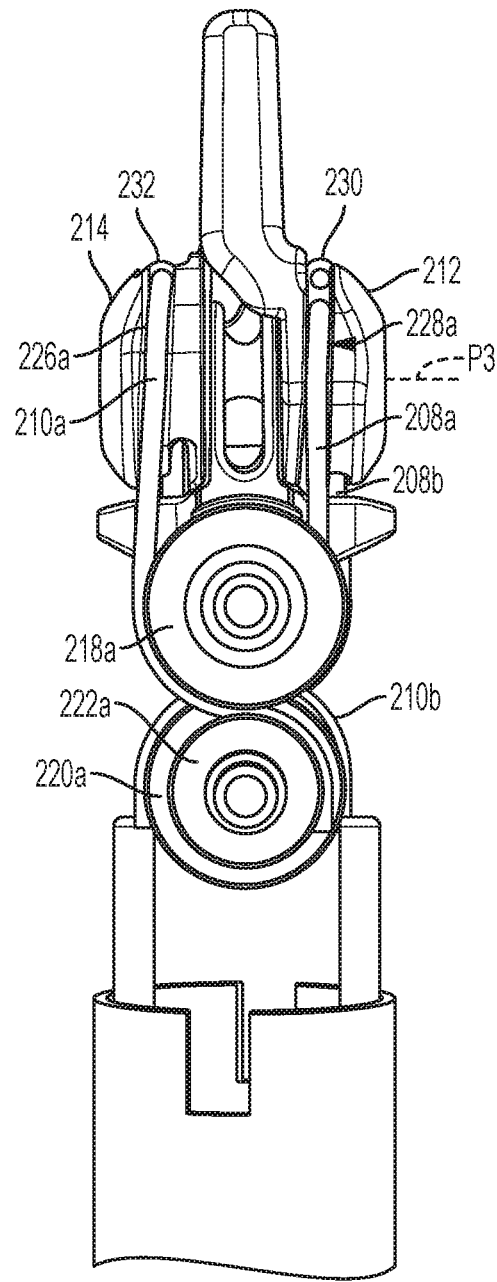
FIG. 19 is another side view of the distal portion of the surgical tool of FIG. 18.
Figure 20:
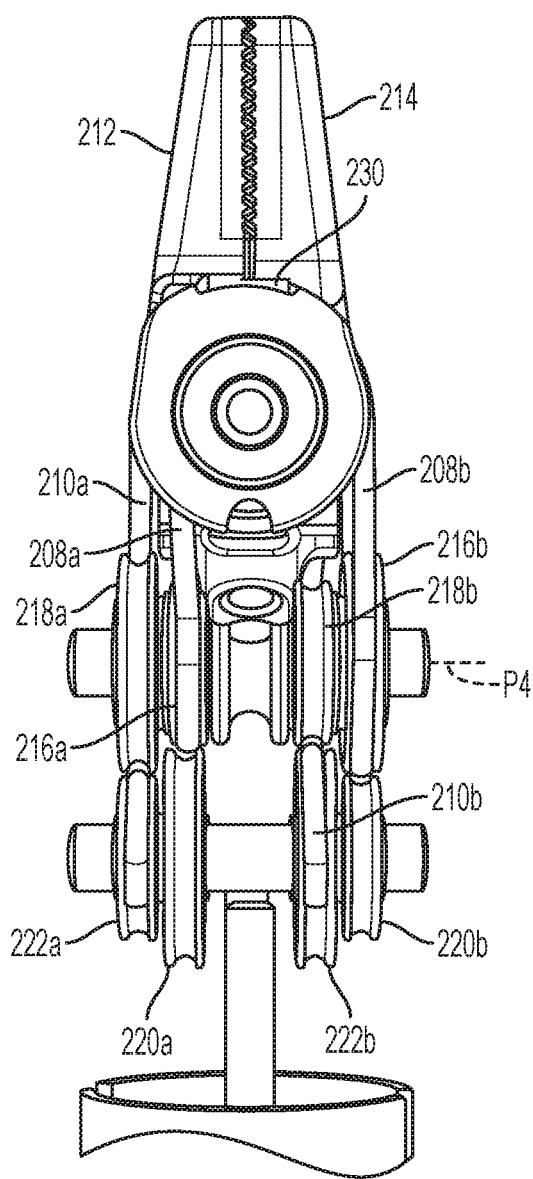
FIG. 20 is yet another side view of the distal portion of the surgical tool of FIG. 18.
Figure 21:
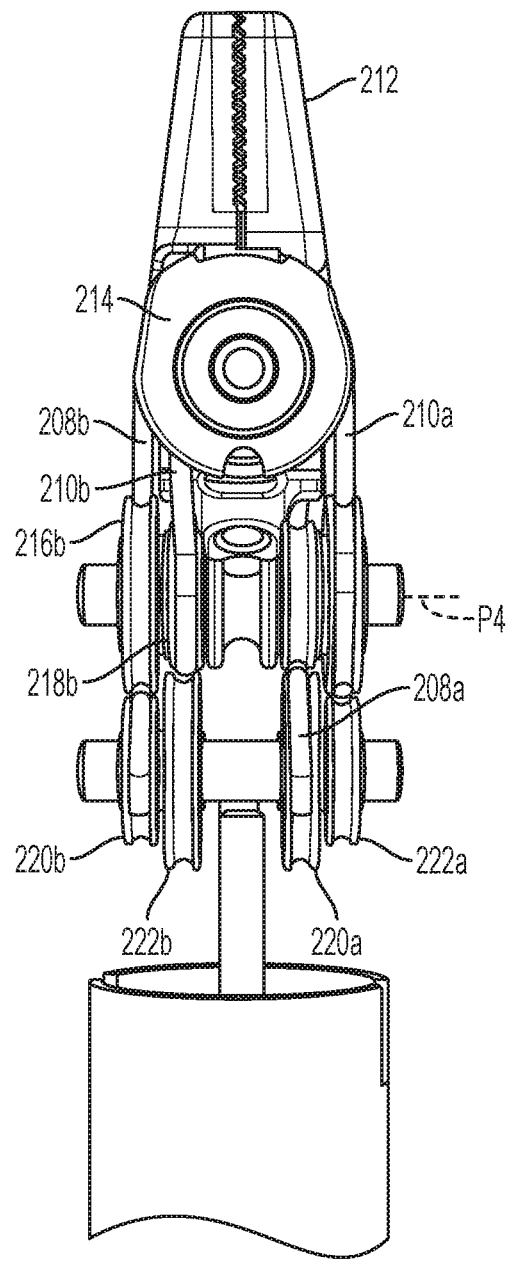
FIG. 21 is still another side view of the distal portion of the surgical tool of FIG. 18.

As shown in FIGS. 18 and 19, the end effector 204 has a plurality of grooves 226a, 226b, 228a, 228b formed therein that each define a helical path and seat therein one of the flexible members 208a, 208b, 210a, 210b. The grooves 226a, 226b, 228a, 228b are configured to guide their respective flexible members 208a, 208b, 210a, 210b to respective ones of the pulleys 216a, 216b, 218a, 218b at a substantially zero fleet angle regardless of whether or not the end effector 204 is articulated and, if the end effector 204 is articulated at a non-zero angle relative to the shaft's longitudinal axis, regardless of the non-zero angle at which the end effector 204 is articulated. In this illustrated embodiment, the flexible members 208a, 208b, 210a, 210b bend at their respective ones of the first plurality of pulleys 216a, 216b, 218a, 218b to curve to an opposite side of the end effector 204 to engage one of the second plurality of pulleys 220a, 220b, 222a, 222b that are located proximal to the first plurality of pulleys 216a, 216b, 218a, 218b. The bending of the flexible members 208a, 208b, 210a, 210b to an opposite side of the tool 200 may help maintain the flexible members' substantially zero angle approach to and engagement with the second plurality of pulleys 220a, 220b, 222a, 222b when the end effector 204 is articulated.

Figure 22:
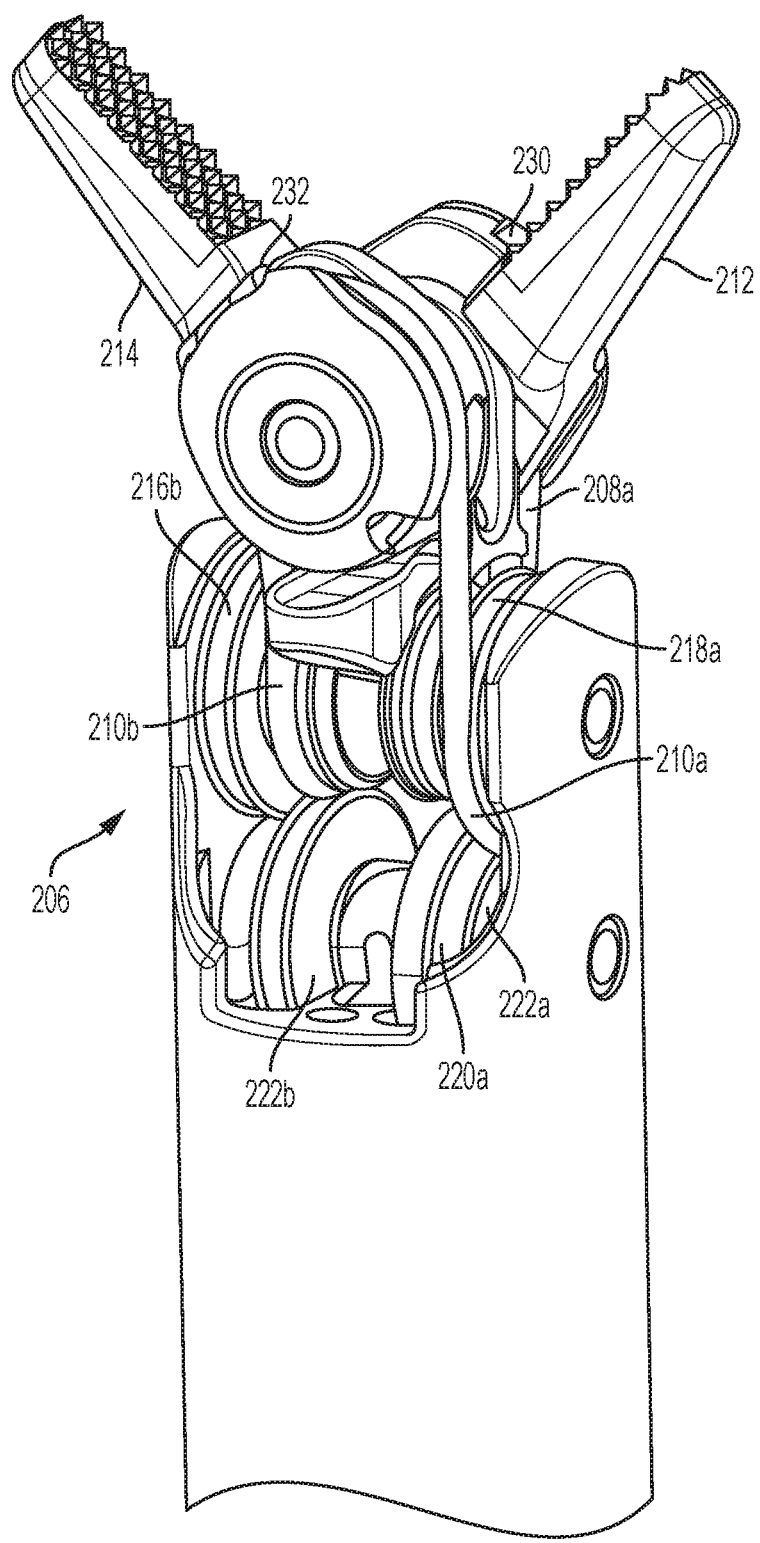
FIG. 22 is a perspective view of a distal portion of the surgical tool of FIG. 17 with the end effector unarticulated and in an open position.
Figure 23:
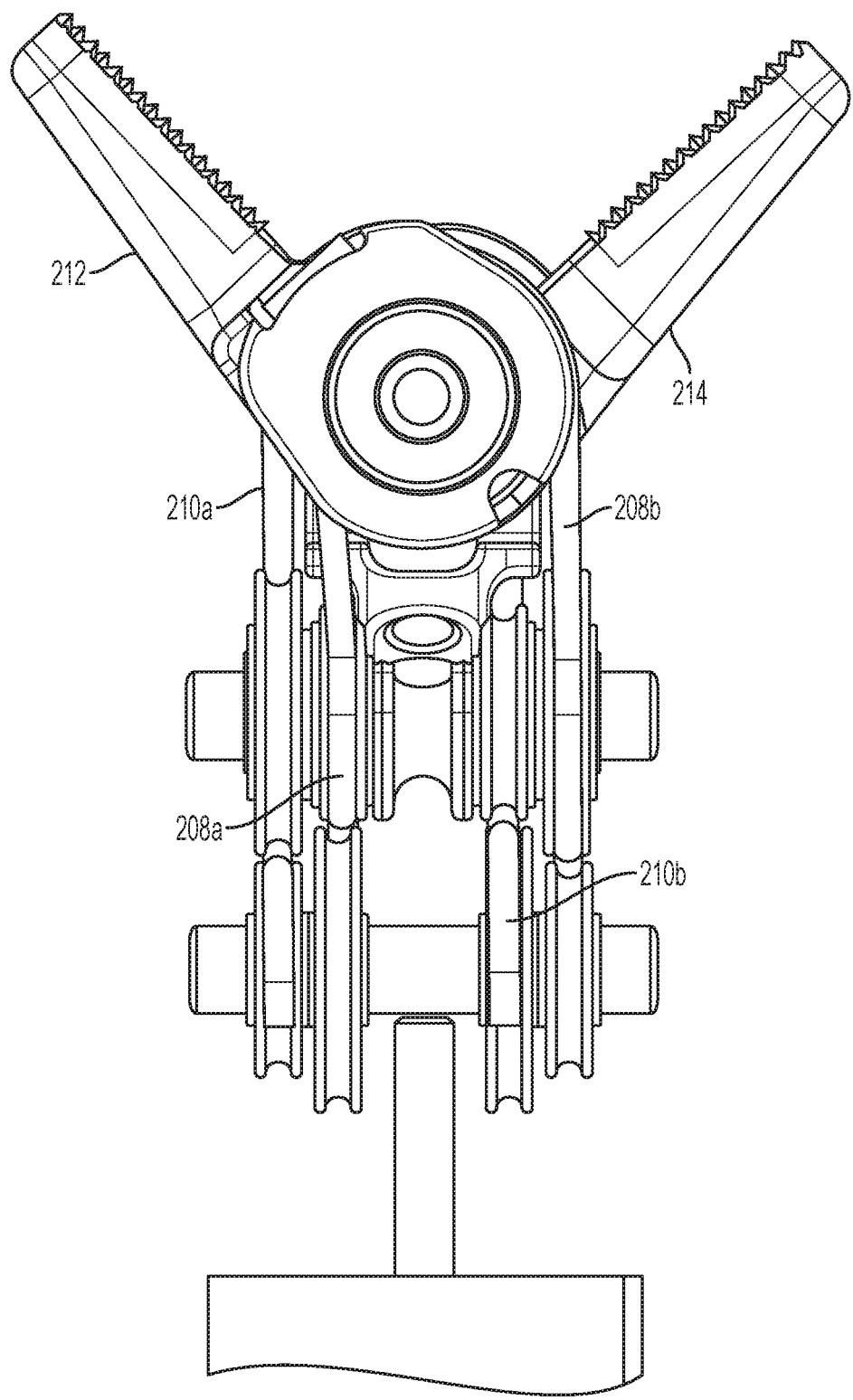
FIG. 23 is a side view of a distal portion of the surgical tool of FIG. 22 with the distal portion of the shaft of the surgical tool omitted for clarity of illustration.
Figure 24:
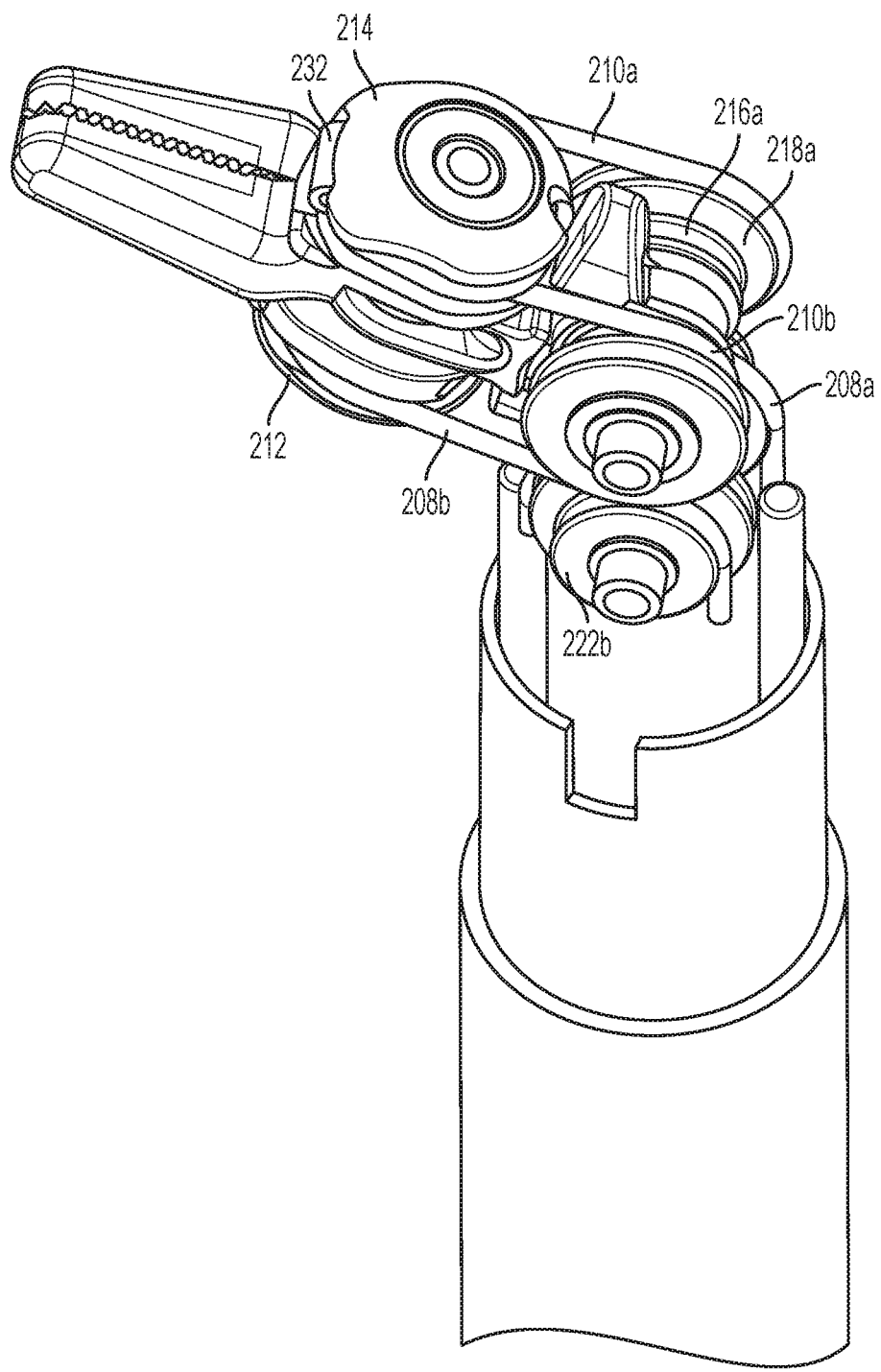
FIG. 24 is a perspective view of a distal portion of the surgical tool of FIG. 17 with the end effector articulated in one degree of freedom and in the closed position with the distal portion of the shaft of the surgical tool omitted for clarity of illustration.
Figure 25:
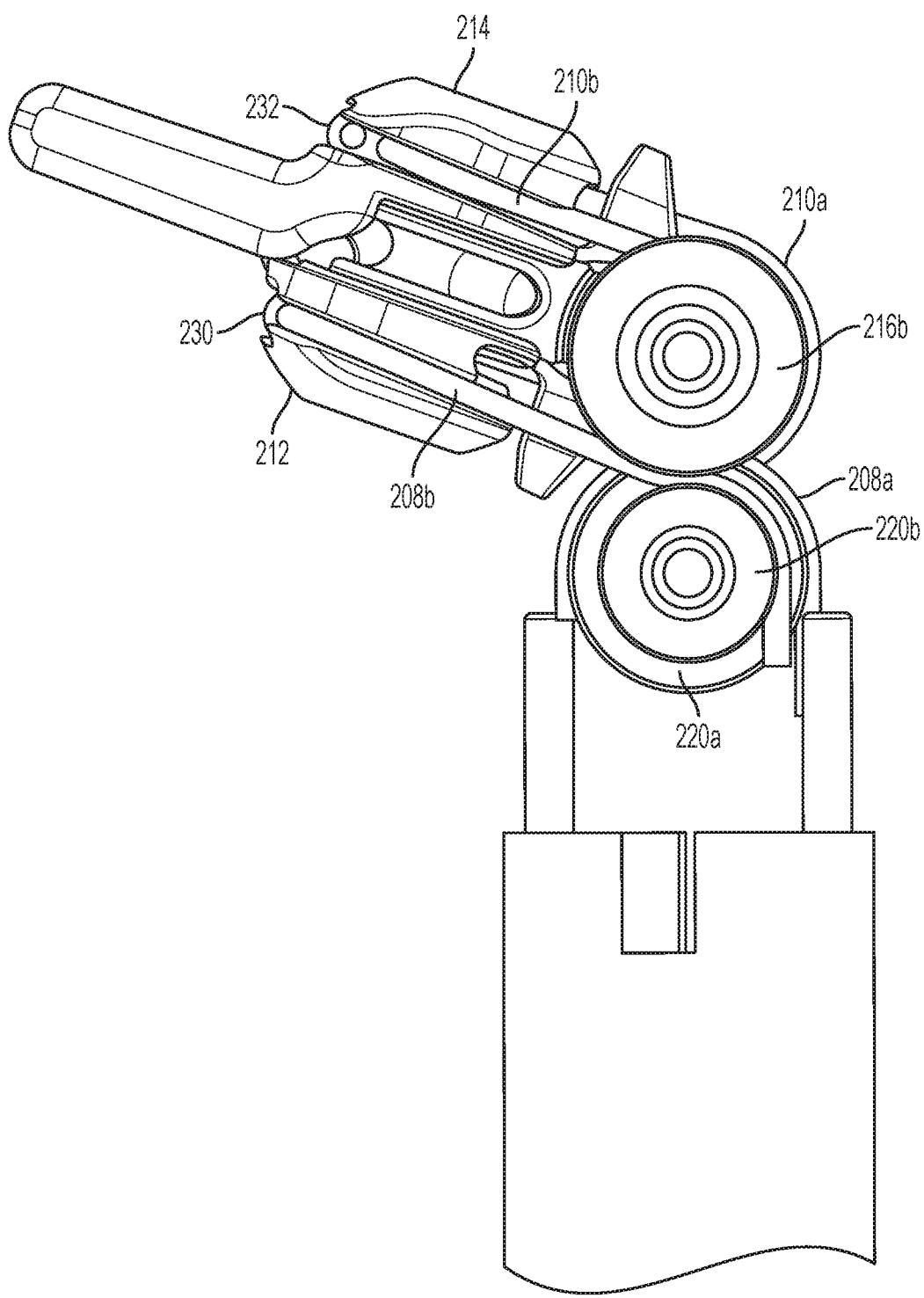
FIG. 25 is a side view of the distal portion of the surgical tool of FIG. 24.
Figure 26:
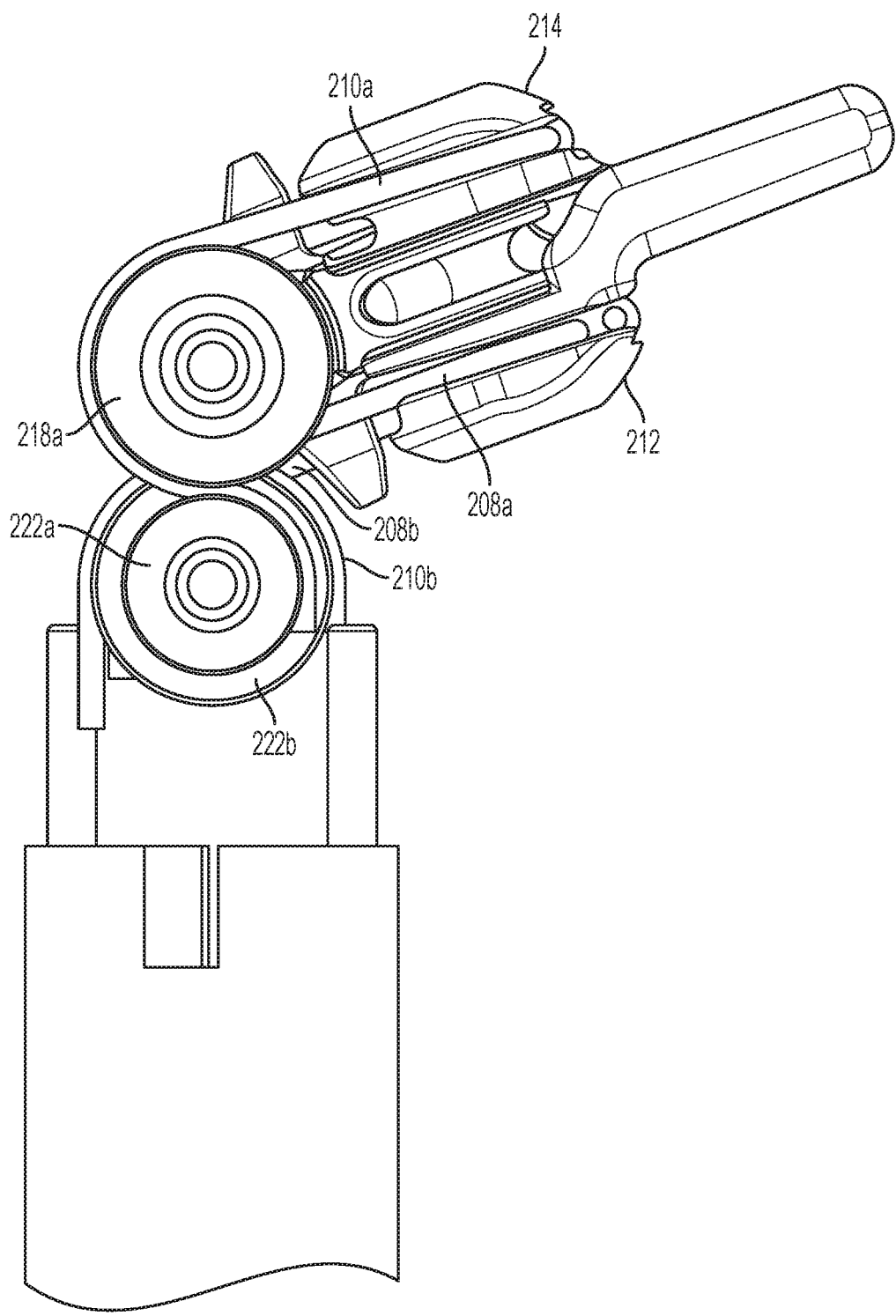
FIG. 26 is another side view of the distal portion of the surgical tool of FIG. 24.
Figure 27:
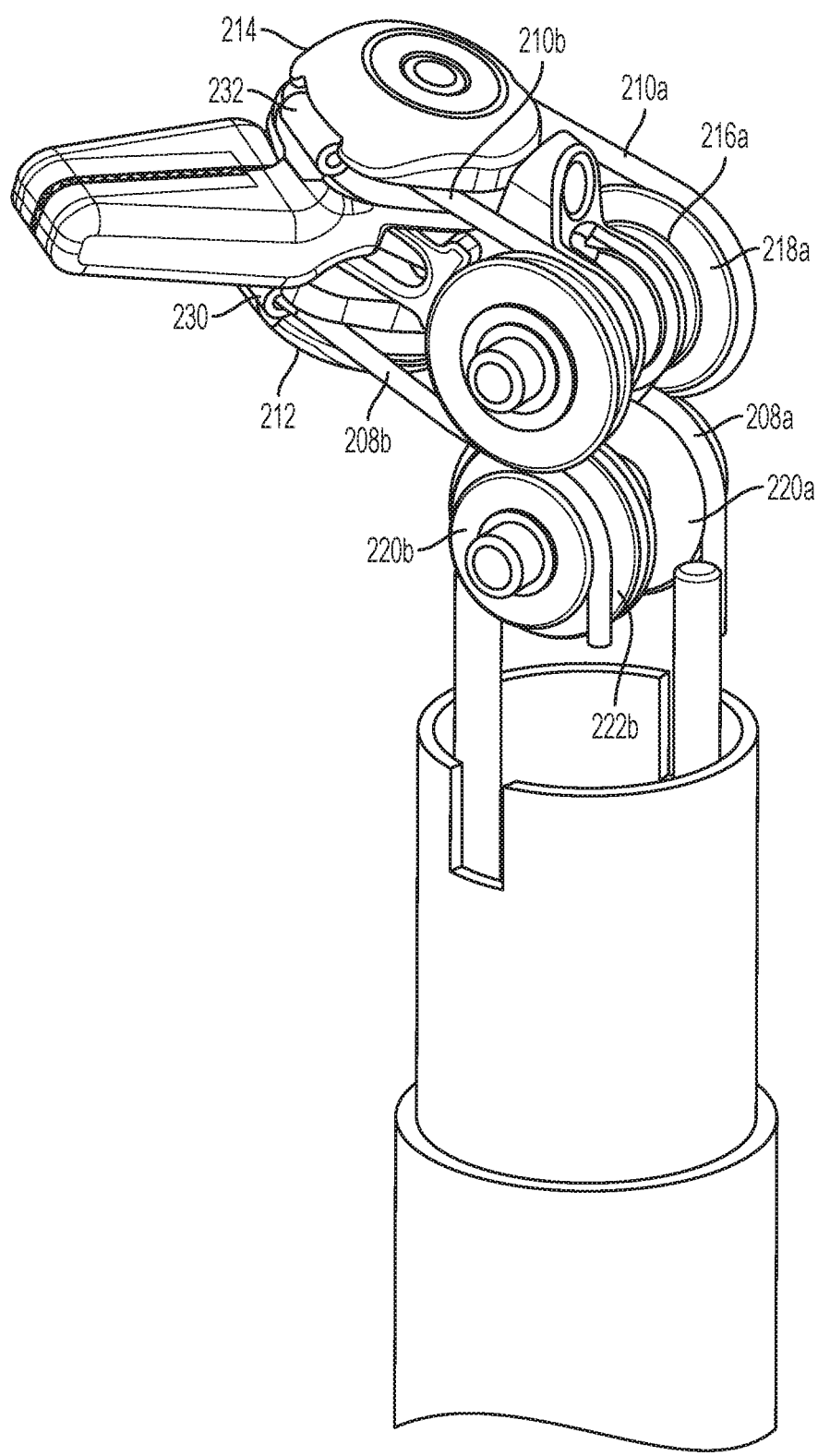
FIG. 27 is a perspective view of a distal portion of the surgical tool of FIG. 17 with the end effector articulated in two degrees of freedom and in the closed position with the distal portion of the shaft of the surgical tool omitted for clarity of illustration.
Figure 28:
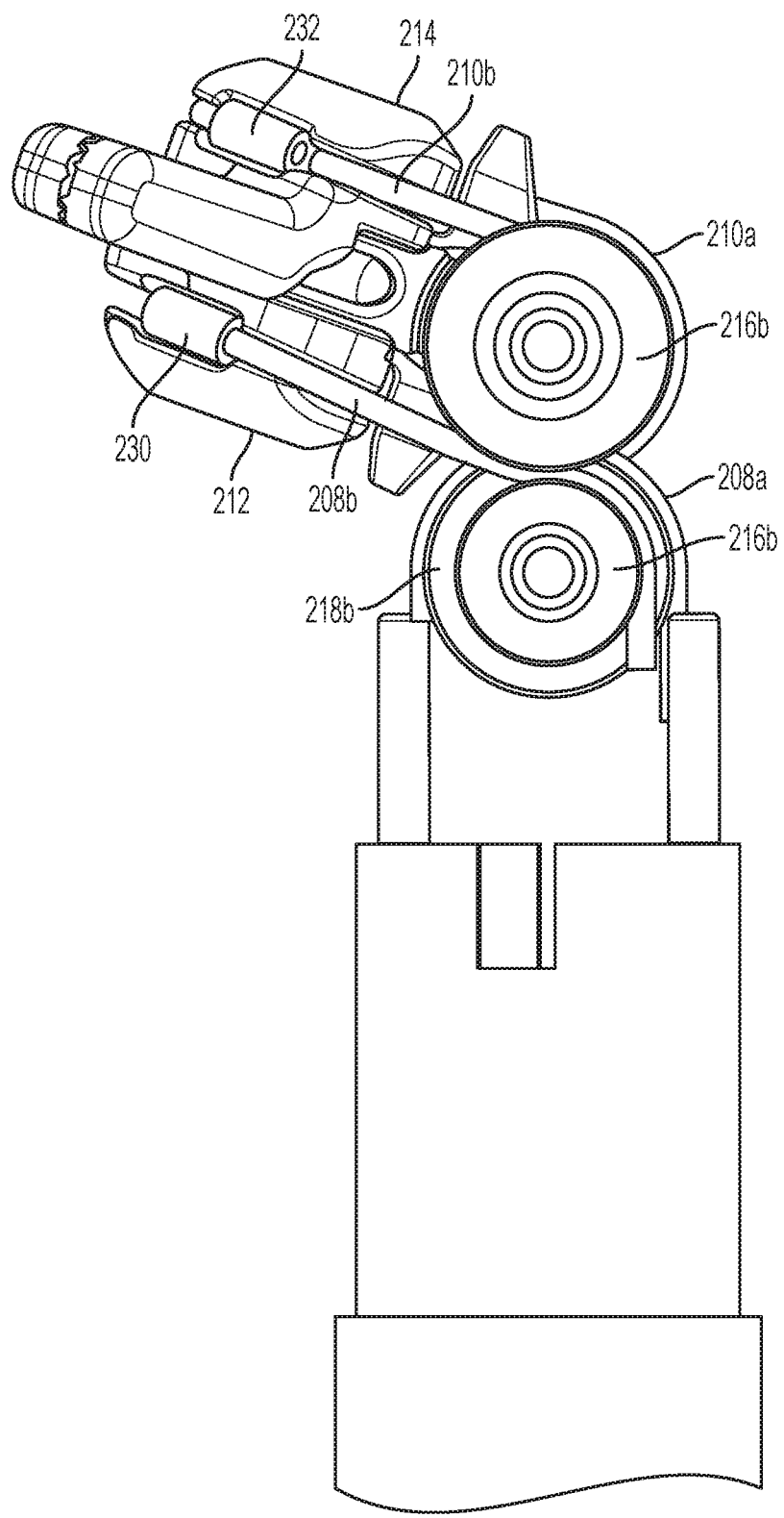
FIG. 28 is a side view of the distal portion of the surgical tool of FIG. 27.
Figure 29:
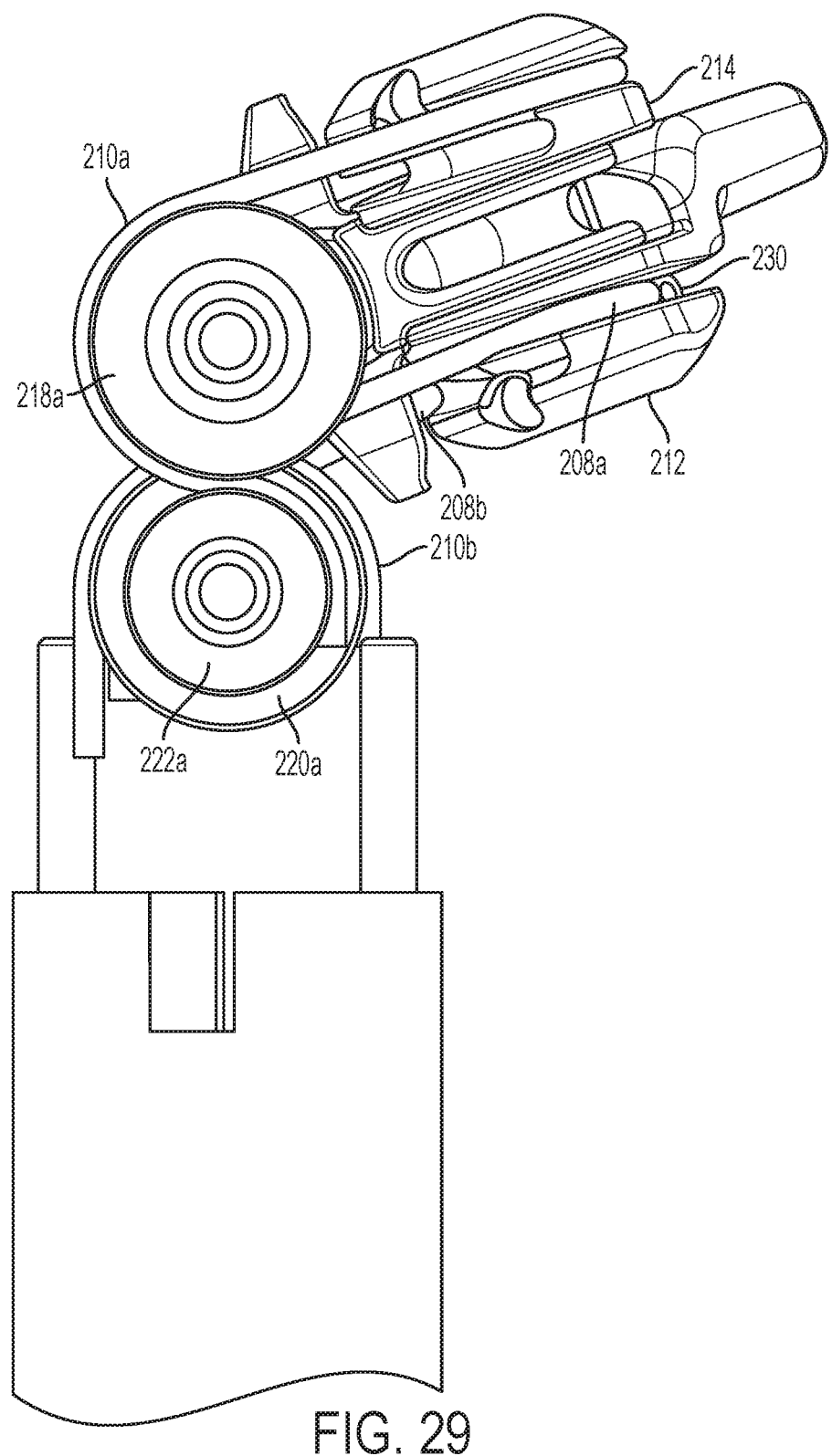
FIG. 29 is another side view of the distal portion of the surgical tool of FIG. 27.

FIGS. 18-21 illustrate the end effector 204 unarticulated and in a closed position, e.g., with the jaws 212, 214 closed together. FIGS. 22 and 23 illustrate the end effector 204 unarticulated and in an open position, e.g., with the jaws 212, 214 spaced apart from one another. FIGS. 22 and 23 show that with the jaws 212, 214 open, the flexible members 208a, 208b, 210a, 210b approach and engage their respective ones of the pulleys 216a, 216b, 218a, 218b, 220a, 220b, 222a, 222b at a substantially zero angle. FIGS. 24-26 illustrate the end effector 204 in the closed position and articulated with one degree of freedom. The end effector 204 is articulated about the second pivot axis P4 (e.g., pitch movement) and is unarticulated about the first pivot axis P3 (e.g., no yaw movement). FIGS. 24-26 show that with the jaws 212, 214 articulated in one degree of freedom, the flexible members 208a, 208b, 210a, 210b approach and engage their respective ones of the pulleys 216a, 216b, 218a, 218b, 220a, 220b, 222a, 222b at a substantially zero angle. The end effector 204 being articulated in one degree of freedom and in the open position would result in similar flexible member approach and engagement. FIGS. 27-29 illustrate the end effector 204 in the closed position and articulated with two degrees of freedom. The end effector 204 is articulated about the second pivot axis P4 (e.g., pitch movement) and about the first pivot axis P3 (e.g., yaw movement). FIGS. 27-29 show that with the jaws 212, 214 articulated in two degrees of freedom, the flexible members 208a, 208b, 210a, 210b approach and engage their respective ones of the pulleys 216a, 216b, 218a, 218b, 220a, 220b, 222a, 222b at a substantially zero angle. The end effector 204 being so articulated and in the open position would result in similar flexible member approach and engagement.

Figure 30:
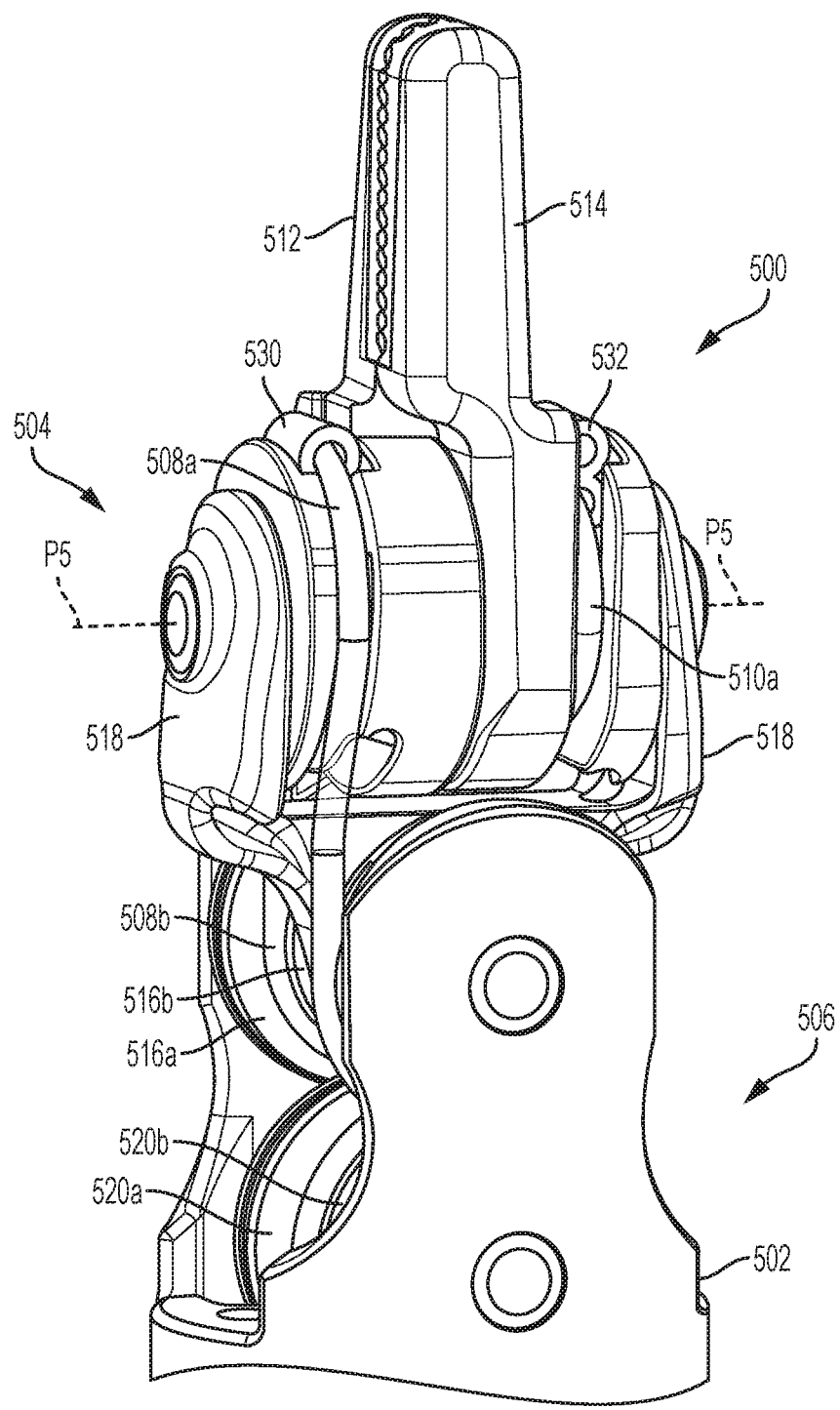
FIG. 30 is a perspective view of yet another embodiment of a surgical tool having a wrist and with an end effector of the surgical tool unarticulated and in a closed position.

FIG. 30 illustrates yet another exemplary embodiment of a surgical tool 500 that includes an elongate shaft 502, an end effector 504 including a pair of opposed jaws 512, 514, a wrist 506 that couples the end effector 504 to the shaft 502 at a distal end of the shaft 502, a plurality of elongate flexible members 508a, 508b, 510a (a fourth elongate flexible member is obscured in FIG. 30), first and second double barrel members 530, 532, a first plurality of pulleys 516a, 516b (two more of the first plurality of pulleys are obscured in FIG. 30) at the wrist 506, and a second plurality of pulleys 520a, 520b (two more of the second plurality of pulleys are obscured in FIG. 30) at the wrist 506. The tool 500 is generally configured and used similar to the tool 100 of FIG. 3. The tool 500 can include a tool housing (not shown) coupled to a proximal end of the shaft 502. The tool 500 has two joints at a first pivot axis P5, one joint for each of the jaws 512, 514. In this illustrated embodiment, a coupling member 518 coupled to the jaws 512, 514 extends to each of the joints, which is in contrast to a coupling member that does not extend to joints at the pivot axis about which jaws are configured to pivot relative to each other, such as a coupling member 134 of the tool 100 of FIGS. 3 and 5 that does not extend to the joints at the pivot axis P1. The coupling member 518 extending to the joints may help provide stability of jaw movement and/or may improve overall end effector 504 stability.

Figure 31:
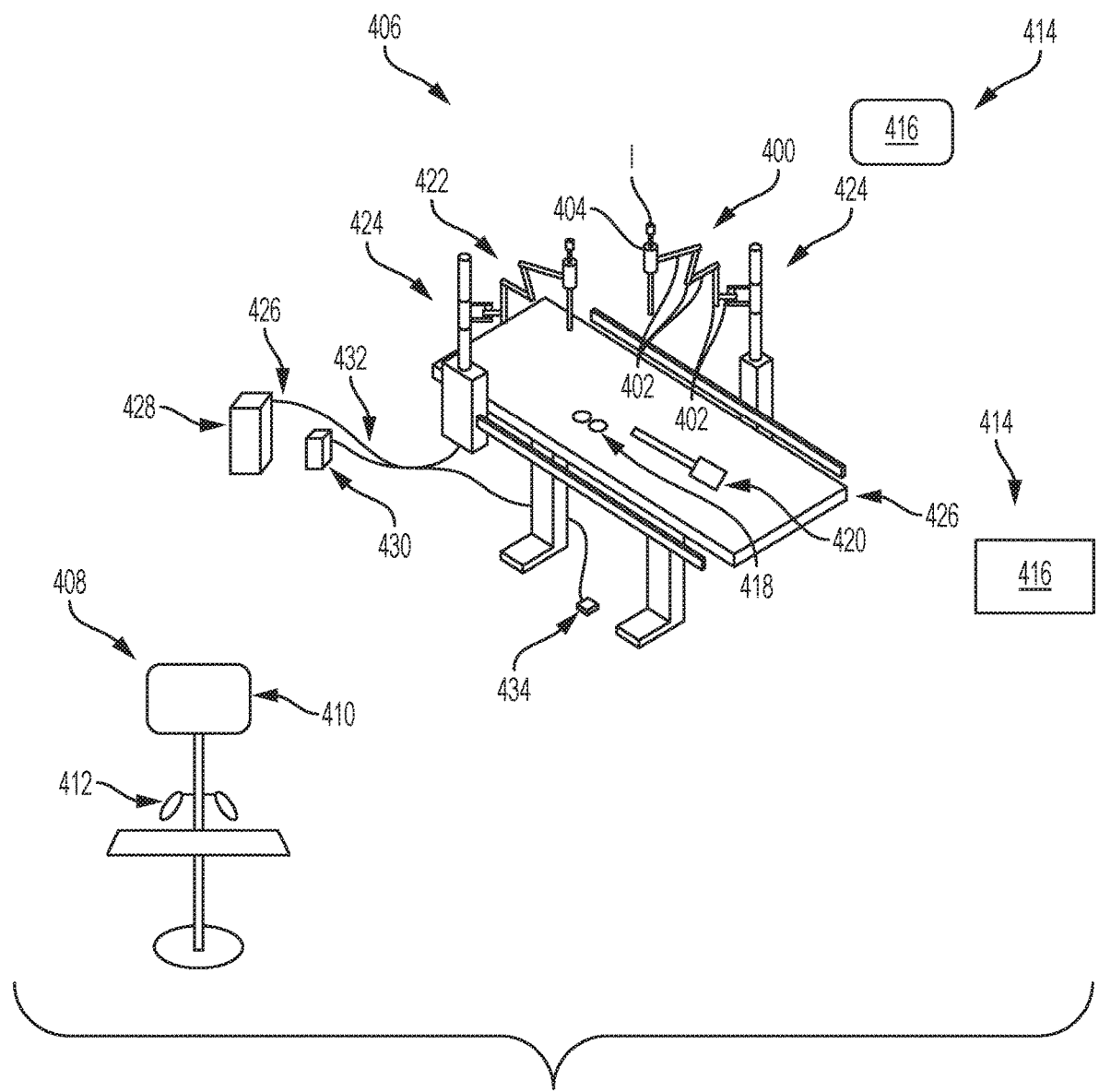
FIG. 31 is a schematic view of one embodiment of a robotic surgical system configured to be operated by a user and to be used during performance of a surgical procedure on a patient.
Figure 32:
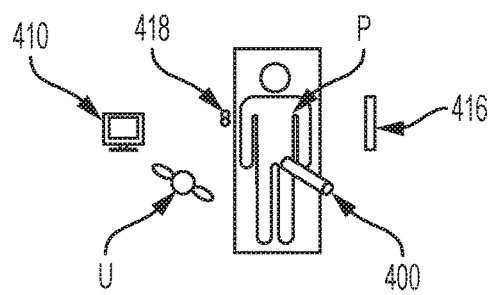
FIG. 32 is a schematic view of one embodiment of the robotic surgical system of FIG. 31 in use during performance of a surgical procedure on a patient.

FIGS. 31 and 32 illustrate one embodiment of a robotic surgical system 406 configured to facilitate performance of a surgical procedure on a patient P and to be releasably coupled to any of the embodiments of surgical tool disclosed herein. The robotic surgical system 406 includes an arm 400 in the form of an electromechanical arm. The electromechanical arm 400 includes one or more mechanical members 402 configured to move in response to an electronic input. Examples of mechanical members that can form the arm include elongate shafts, coupling mechanisms (e.g., clips, magnets, snap fit mechanisms, shaped members configured to seat an instrument therein by interference fir or press fit, clamps, protrusions configured to be seated in corresponding depressions formed in a surgical instrument, depressions configured to receive therein corresponding protrusions extending from a surgical instrument, etc.) configured to removably and replaceably couple a surgical instrument to the arm, and joints (e.g., hinges, gimbals, etc.). The arm 400 also includes a plurality of joints between adjacent mechanical members 402, and a coupling mechanism 404 configured to removably and replaceably couple to a surgical instrument I that can include one of the surgical tools disclosed herein. The arm 400 includes five mechanical members 402 and four joints in this illustrated embodiment, but arms can have any number of mechanical members and associated joints.

Figure 33:
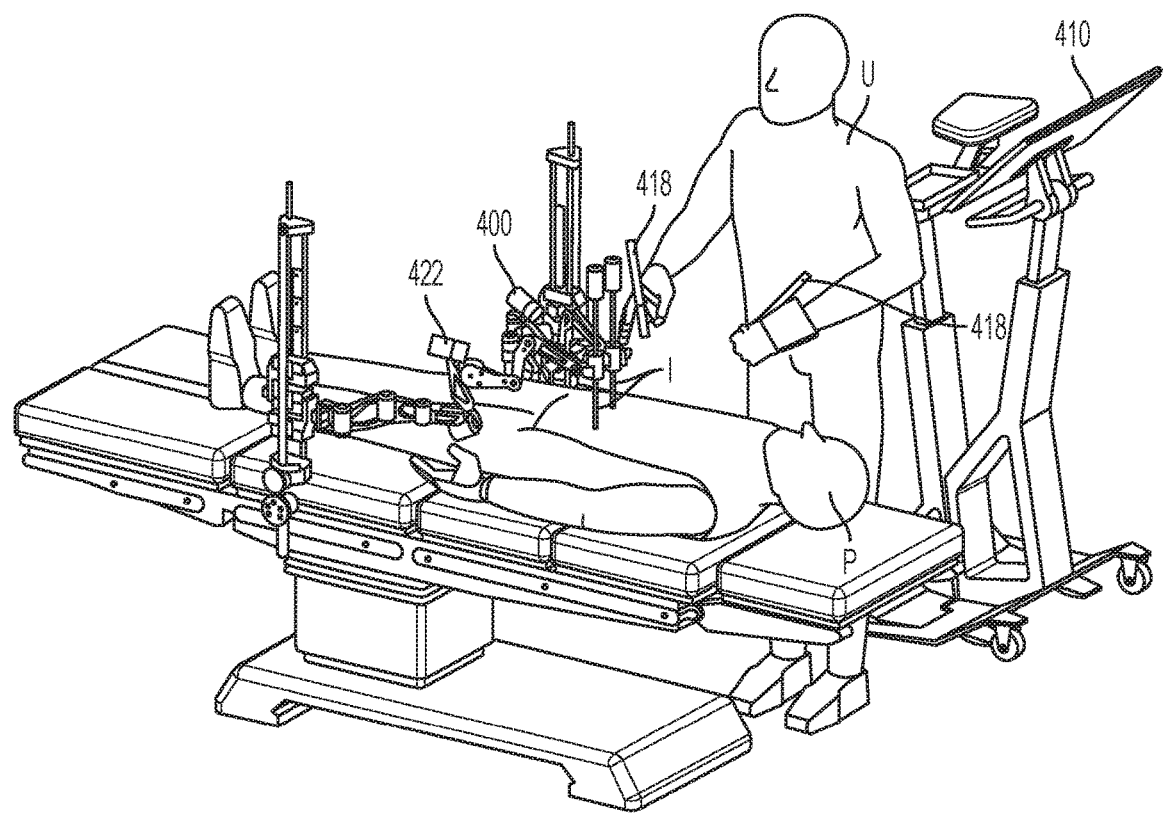
FIG. 33 is a perspective view of the robotic surgical system of FIG. 32 in use during performance of the surgical procedure on a patient.

FIG. 33 shows one embodiment of the system 406 in use. The system 406 includes a user interface sub-system 408 that includes at least one display 410 configured to display information thereon to a user U, at least one user input device 412 configured to receive a user input thereto to control movement of the arm 400, a visualization system 414 that includes at least one display 416 configured to display thereon image(s) of a surgical procedure being performed using the system 406, a freely movable user input device 418 (shown as pinchers in this illustrated embodiment) configured to receive a user input thereto to control movement of the arm 400 and configured to be freely moved around by the user U (e.g., handheld and moved around any space in or near an operating room, etc.), an additional arm 422 configured and used similar to the arm 400, and a control system 426 configured to facilitate control of the arms 400, 422 by translating user inputs to the user input devices 412, 418, e.g., manual movement of a user input device, movement indicated by touch on a touch screen, etc., to one or both of the arms 400, 422 as appropriate. The system 406 in this illustrated embodiment includes two arms 400, 422, but it can include another number of arms, e.g., three, four, etc. The at least one display 410 of the user interface sub-system 408 can be configured as a user input device, e.g., as a touchscreen configured to receive user touch input thereon. The user interface sub-system 408 can be in the same room as the patient P, or it can be in a different room.

The control system 426 includes at least one computer system 428, one or more cables 432, and at least one power supply 430. The computer system 428 includes at least one processor (not shown). At least some embodiments of control systems can be at least partially wireless, in which case at least some of the cables 432 need not be present. The robotic surgical system 406 includes at least one foot pedal 434 coupled to the computer system 428 via one of the cables 432, which can allow the foot pedal 434 to serve as a user input device. The robotic surgical system 406 can include at least one knee control (not shown) coupled to the computer 428 via one of the cables 432, similar to a knee control of a sewing machine, which can allow the knee control to serve as a user input device.

The robotic surgical system 406 includes a frame 424 for each of the arms 400, 422. The frames 424 in this illustrated embodiment are each mounted to a surgical table 426, but the frames 424 can be mounted elsewhere. The frames 424 in this illustrated embodiment include a vertical extension movably coupled to a rail mounted to the table 426. The vertical extension is configured to move along the rail, thereby facilitating positioning of the arms 400, 422 relative to the patient P.

One or more manually operated surgical instruments 420, e.g., instruments not under the control of the robotic surgical system 406, are also being used to perform the surgical procedure being performed on the patient P. In other embodiments, no manual instruments 420 are used.

Aspects of the robotic surgical system 406 are further described in previously mentioned International Patent Publication No. WO 2014/151621 entitled "Hyperdexterous Surgical System" filed on Mar. 13, 2014.

The systems, devices, and methods disclosed herein can be implemented using one or more computer systems. One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer system having a display device, such as for example a cathode ray tube (CRT) or a liquid crystal display (LCD) or a light emitting diode (LED) monitor for displaying information to the user and a keyboard and an input device, e.g., a mouse, a trackball, a hand tracker, a gesture recognition device (e.g., Kinect), etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 34:
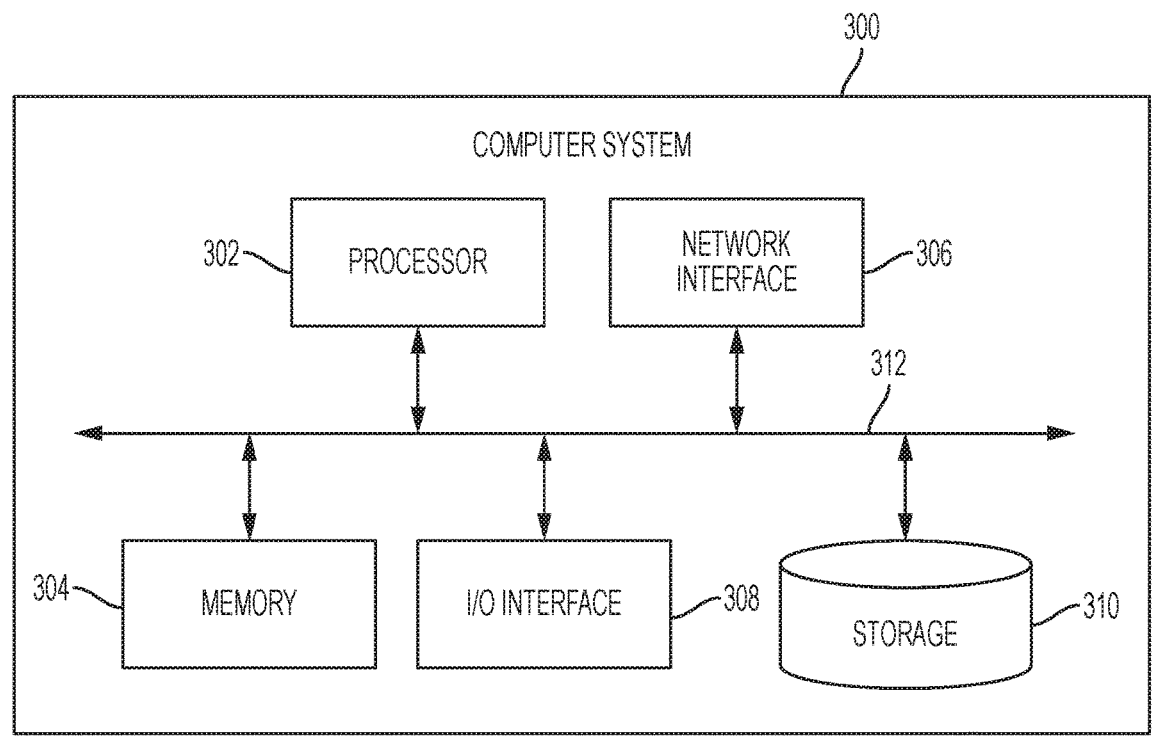
FIG. 34 is a schematic view of one embodiment of a computer system.

FIG. 34 illustrates one exemplary embodiment of a computer system 300. As shown, the computer system 300 can include one or more processors 302 which can control the operation of the computer system 300. "Processors" are also referred to herein as "controllers." The processor(s) 302 can include any type of microprocessor or central processing unit (CPU), including programmable general-purpose or special-purpose microprocessors and/or any one of a variety of proprietary or commercially available single or multi-processor systems. The computer system 300 can also include one or more memories 304, which can provide temporary storage for code to be executed by the processor(s) 302 or for data acquired from one or more users, storage devices, and/or databases. The memory 304 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 300 can be coupled to a bus system 312. The illustrated bus system 312 is an abstraction that represents any one or more separate physical busses, communication lines/interfaces, and/or multi-drop or point-to-point connections, connected by appropriate bridges, adapters, and/or controllers. The computer system 300 can also include one or more network interface(s) 306, one or more input/output (IO) interface(s) 308, and one or more storage device(s) 310.

The network interface(s) 306 can enable the computer system 300 to communicate with remote devices, e.g., other computer systems, over a network, and can be, for non-limiting example, remote desktop connection interfaces, Ethernet adapters, and/or other local area network (LAN) adapters. The IO interface(s) 308 can include one or more interface components to connect the computer system 300 with other electronic equipment. For non-limiting example, the IO interface(s) 308 can include high speed data ports, such as universal serial bus (USB) ports, 1394 ports, Wi-Fi, Bluetooth, etc. Additionally, the computer system 300 can be accessible to a human user, and thus the IO interface(s) 308 can include displays, speakers, keyboards, pointing devices, and/or various other video, audio, or alphanumeric interfaces. The storage device(s) 310 can include any conventional medium for storing data in a non-volatile and/or non-transient manner. The storage device(s) 310 can thus hold data and/or instructions in a persistent state, i.e., the value is retained despite interruption of power to the computer system 300. The storage device(s) 310 can include one or more hard disk drives, flash drives, USB drives, optical drives, various media cards, diskettes, compact discs, and/or any combination thereof and can be directly connected to the computer system 300 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 34 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 300 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 300 can also include a web server for generating and/or delivering the web pages to client computer systems.

In an exemplary embodiment, the computer system 300 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical tool, comprising:
    an elongate shaft;
    an end effector coupled to a distal end of the elongate shaft, the end effector including first and second jaws, the first jaw having a first channel formed in an exterior surface thereof, the second jaw having a second channel formed in an exterior surface thereof, each of the first and second channels extending along a helical path;
    a first elongate flexible member seated in the first channel and configured to be selectively moved to cause movement of the first jaw; and
    a second elongate flexible member seated in the second channel and configured to be selectively moved to cause movement of the second jaw,
    wherein the end effector is movable about a first pivot joint, the first and second jaws are movable relative to one another about a second pivot joint, and the first and second elongate flexible members are configured to be selectively moved to cause movement of the first and second jaws respectively about the second pivot joint, and
    wherein the first jaw includes a third channel formed in the exterior surface thereof, the second jaw includes a fourth channel formed in the exterior surface thereof, and the third and fourth channels each extend along a helical path.

2. The tool of claim 1, further comprising:
    a third elongate flexible member seated in the third channel, the first and third elongate flexible members being configured to be selectively moved to cause movement of the first jaw about the second pivot joint; and a fourth elongate flexible member seated in the fourth channel, the second and fourth elongate flexible members being configured to be selectively moved to cause movement of the second jaw about the second pivot joint.

3. The tool of claim 2, wherein the first channel has a diameter that is greater than a diameter of the third channel, the first and third elongate flexible members have a substantially same diameter, the second channel has a diameter that is greater than a diameter of the fourth channel, and the second and fourth elongate flexible members have a substantially same diameter.

4. The tool of claim 2, wherein the first, second, third, and fourth elongate flexible members are configured to be selectively actuated to articulate the end effector about the first pivot joint.

5. The tool of claim 1,
wherein the end effector is coupled to the elongate shaft at a wrist that includes a first pulley operatively engaged with the first elongate flexible member and a second pulley operatively engaged with the second elongate flexible member.

6. The tool of claim 5, wherein the first elongate flexible member approaches and operatively engages the first pulley at a substantially zero-angle relative to a plane of the first pulley, and the second elongate flexible member approaches and operatively engages the second pulley at a substantially zero-angle relative to a plane of the second pulley.

7. The tool of claim 1, further comprising a housing coupled to a proximal end of the elongate shaft, the housing being configured to couple to a driver of a surgical robot configured to control the movement of the first and second elongate flexible members.

8. The tool of claim 1, wherein each of the first and second elongate flexible members is selected from the group consisting of a cable and a wire.

9. The tool of claim 1, wherein each of the first and second elongate flexible members is a twisted string.

10. A surgical tool, comprising:
an elongate shaft defining a first longitudinal axis;
an end effector coupled to a distal end of the elongate shaft, wherein:
the end effector defines a second longitudinal axis,
the end effector is movable between an articulated position, in which the second longitudinal axis is angularly offset from the first longitudinal axis, and
an unarticulated position, in which the second longitudinal axis is not angularly offset from the first longitudinal axis,
the end effector includes first and second channels, and
with the end effector in the articulated position and with the end effector in the unarticulated position, each of the first and second channels extends along a path that is angularly offset from the second longitudinal axis;
a first elongate flexible member seated in the first channel and configured to be selectively moved to cause movement of the end effector; and
a second elongate flexible member seated in the second channel and configured to be selectively moved to cause movement of the end effector;
wherein the end effector includes a first jaw having the first channel formed in an exterior surface thereof;
the first jaw has a third channel formed in the exterior surface thereof;
the end effector includes a second law having the second channel formed in an exterior surface thereof;
the second jaw has a fourth channel formed in the exterior surface thereof; and
the tool further comprises:
a third elongate flexible member seated in the third channel, the first and third elongate flexible members being configured to be selectively moved to cause movement of the first jaw, and
a fourth elongate flexible member seated in the fourth channel, the second and fourth elongate flexible members being configured to be selectively moved to cause movement of the second jaw.

11. The tool of claim 10, further comprising a first pulley having a fifth channel formed therein, and a second pulley having a sixth channel formed therein;
wherein the first elongate flexible member approaches and operatively engages the first pulley at a substantially zero-angle relative to a plane of the first pulley, and the second elongate flexible member approaches and operatively engages the second pulley at a substantially zero-angle relative to a plane of the second pulley.

12. The tool of claim 10, further comprising a housing coupled to a proximal end of the elongate shaft, the housing being configured to couple to a driver of a surgical robot configured to control the movement of the first and second elongate flexible members.

* * * * *